United States Patent
Du et al.

(10) Patent No.: US 9,816,101 B2
(45) Date of Patent: Nov. 14, 2017

(54) DROUGHT AND SUBMERGENCE TOLERANCE IN PLANTS

(71) Applicant: THE REGENTS OF THE UNIVERSITY OF CALIFORNIA, Oakland, CA (US)

(72) Inventors: Hewei Du, Davis, CA (US); Yufan Zhou, Davis, CA (US); Nir Oksenberg, Davis, CA (US); Pamela Ronald, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/839,741

(22) Filed: Aug. 28, 2015

(65) Prior Publication Data

US 2016/0068855 A1 Mar. 10, 2016

Related U.S. Application Data

(60) Provisional application No. 62/112,572, filed on Feb. 5, 2015, provisional application No. 62/043,335, filed on Aug. 28, 2014.

(51) Int. Cl.
*C12N 15/82* (2006.01)

(52) U.S. Cl.
CPC ................ *C12N 15/8273* (2013.01)

(58) Field of Classification Search
None
See application file for complete search history.

(56) References Cited

U.S. PATENT DOCUMENTS

2007/0192889 A1* 8/2007 La Rosa ............ C07K 14/415
800/278

OTHER PUBLICATIONS

Fukao et al. Evolutionary analysis of the Sub1 gene cluster that confers submergence tolerance to domesticated rice. Annals of Botany 103: 143-150, 2009.*
Kaplan-Levy et al. The trihelix family of transcription factors—light, stress and development. Trends Plant Sci. Mar. 2012;17(3):163-71. Epub Jan. 10, 2012.*
Boyer et al. The SANT domain: a unique histone-tail-binding module? Nature Reviews Molecular Cell Biology 5, 158-163 (Feb. 2004.*
Whisstock J.C. et al. Prediction of protein function from protein sequence and structure. Q Rev Biophys. Aug. 2003;36(3):307-40. Review.*
Seo et al. Towards establishment of a rice stress response interactome. PLoS Genet. Apr. 2011;7(4):e1002020. pp. 1-12. Epub Apr. 14, 2011.*

\* cited by examiner

*Primary Examiner* — Cynthia Collins
(74) *Attorney, Agent, or Firm* — Kilpatrick Townsend & Stockton LLP

(57) ABSTRACT

The invention provides methods of genetically modified plants to increase tolerance to drought and/or submergence. The invention additionally provides plants having increased drought and/or submergence tolerance engineered using such methods.

17 Claims, 8 Drawing Sheets

Figure 1

CLUSTAL 2.1 multiple sequence alignment-SAB18 polypeptides

```
GRMZM2G126148_T02|PACid_208616    ------------------------------------------------------------ME
LOC_Os11g06410.1                  MSILLWLSHVLLKLHYLRLYSCASSCTPVSILYGTNKKLKCLGDRFGEME
Sb08g003990.1|PACid_1977601       ------------------------------------------------------------ME
Si010104m|PACid_19697305          ------------------------------------------------------------ME
AC234952_14.1|PACid_23053207      ------------------------------------------------------------ME
Potri.002G068700.1|PACid_27020    ------------------------------------------------------------ME
AT1G76870.1                       ------------------------------------------------------------ME
Bradi2g12030.1|PACid_21804939     ------------------------------------------------------------MG
SAB18OX LINE SEQ ID NO:6          MSILLWLSHVLLKLHYLRLYSCASSCTPVSILYGTNKKLKCLGDRFGEME
                                                                                    *

GRMZM2G126148_T02|PACid_208616    GNDLPPGNMLQG-APYDSLDLHGD-SMAKHAPNSGKQIFSSSQMPGTFTM
LOC_Os11g06410.1                  GSN-PPGNMTQG-PSYGSLDLHGI-SKQMHPPNSGNQGFNQPQIPGNFTI
Sb08g003990.1|PACid_1977601       GNNLPSGSLMQG-AAYGNLDLHHSHMQMPAPSSGNQAFNHSQMPANFPI
Si010104m|PACid_19697305          GNNLPSGSLMQG-TNYGSLDLHHN-HMQMHAPNSGNQGFNHSQMPSNFPI
AC234952_14.1|PACid_23053207      GNLSQGGIVQGGGGSFGGFDLPGS--MRVHRGQHPHTMNQHQAHPC-QG
Potri.002G068700.1|PACid_27020    GNLSQGGMIPGG-APFGGLDLQGS---MRVHHQAQHPHTMHHQHPLHRQG
AT1G76870.1                       GNCSQG-------RFD--SQVSS--MRDLR----PNAINQNQKQHH---
Bradi2g12030.1|PACid_21804939     PRGAPAAMLGMGMQQFVSQPHAAAPVFQQPEHLHGGVFGQHHHQPVPAPA
SAB18OX LINE SEQ ID NO:6          GSN-PPGNMTQG-PSYGSLDLHGI-SKQMHPPNSGNQGFNQPQIPGNFTI
                                                  :

GRMZM2G126148_T02|PACid_208616    SMTRATEPDDFP-GFQFKEHGKSDDHHHHQYHSHHQKNCMSDGEEHD---
LOC_Os11g06410.1                  PMDRVTEPDNISDGVQLGQHGKIAHHHH--HRHHSKNHGSDEEEHD---
Sb08g003990.1|PACid_1977601       CLNQVTDSDQLP-EFQFGEHGKVSHHHHHHHHQQHAKNSMSDDEEHG---
Si010104m|PACid_19697305          HLNQVTDSDQLS-EFQFGEHGKAN-HHHQHHNQQHTKISMSDDEEHG---
AC234952_14.1|PACid_23053207      PAVHSSINEGFPLTMGTLKNCDQTMSMNEFSQGDRNKHSGSEEDEP---E
Potri.002G068700.1|PACid_27020    SSTLTSVEEGFPLTMGFMHNSDQNISMTDYNKGDRGKNSVSDEDEPSYTE
AT1G76870.1                       --PNSRQDSGFNNTMDTRHN---------NVDRGKKSMSEDDELC--L
Bradi2g12030.1|PACid_21804939     RQQPPSYSPYPAVPVRAGGG---------HHEEEAMGHGAGND---
SAB18OX LINE SEQ ID NO:6          PMDRVTEPDNISDGVQLGQHGKIAHHHH--HRHHSKNHGSEEEEHD---
                                                    :    ..

GRMZM2G126148_T02|PACid_208616    MAEDATDTPSGKGKKKGSAWHRMKWTDSMVKLLITAVSYTGDDH------
LOC_Os11g06410.1                  MNEDAAD---GKDKKGSPWHRMKWTDSMVKLLITAVSYTGEDP-------
Sb08g003990.1|PACid_1977601       VHEDATDSQTSKGKKGSAWHRMKWTDSMVRLLITAASYAGEDP-------
Si010104m|PACid_19697305          VNEDATDSQTGKGKKGSAWHRMKWTDSMVKLLITAASYTGEDP-------
```

Figure 1 - cont.

```
AC234952_14.1|PACid_23053207              EGGDGHHQEGSRGKKGSPWQRVKWTDKMVRLLITAVSYIGEDG------------
Potri.002G068700.1|PACid_27020            EGADGHN-DAITGKKGTPWQRVKWTDKMVRLLITAVSYIGEDG------------
AT1G76870.1                               LSSDGQN----KSKENSPWQRVKWMDKMVKLMITALSYIGEDS------------
Bradi2g12030.1|PACid_21804939             -GVAAQQ----QQQPGGLWSRMKWTDAMVRLLIMVVYNAGDDGEGAVAAA-----
SAB18OX LINE SEQ ID NO:6                  MNEEDAAD---GKDKKGSPWHRMKWTDSMVKLLITAVSYTGEDP-----------
                                                        *  *:**  * **:*:*  .

GRMZM2G126148_T02|PACid_208616            -GAD-SGGGRRNIAITQ-------------KKGKWKAISKVMGERGCHVS
LOC_Os11g06410.1                          -GAD-LGGGRRNYSMMQ-------------KKGKWKAISKVMGERGCHVS
Sb08g003990.1|PACid_1977601               -GAD-LGGGRRSCAMMQ-------------KKGKWKAISKVMGERGCLVS
Si010104m|PACid_19697305                  -GAD-SGG-RRNCAMMQ-------------KKGKWKAISKVMGQRGCLVS
AC234952_14.1|PACid_23053207              -SSEGGSGGRRKFAVLQ-------------KKGKWKSISKVMAERGYRVS
Potri.002G068700.1|PACid_27020            -TSDCGGGMRRKFTVLQ-------------KKGKWKSVSKVMARRGFHVS
AT1G76870.1                               -GSD------KKFAVLQ-------------KKGKWRSVSKVMDERGYHVS
Bradi2g12030.1|PACid_21804939             VGGGGGGGSRAAAHGHGHGSATAAAHAQQKKGKWKSVSRTMGEHGFTVS
SAB18OX LINE SEQ ID NO:6                  -GAD-LGGGRRNYSMMQ-------------KKGKWKAISKVMGERGCHVS
                                             .             :             ****.*   :*  * *

GRMZM2G126148_T02|PACid_208616            PQQCEDKFNDLNKRYKRLIDILGMGTACNVVANPALLDSMNHLSDKMKDN
LOC_Os11g06410.1                          PQQCEDKFNDLNKRYKRLTDILGRGTACNVVENHSLLDHMD-ISEKMKED
Sb08g003990.1|PACid_1977601               PQQCEDKFNDLNKRYKRLTDILGRGTTCRVVANPELLDGMTNLSDKMKDD
Si010104m|PACid_19697305                  PQQCEDKFNDLNKRYKRLTDLLGRGTTCRIVANPELLDSMANLSDKTKDD
AC234952_14.1|PACid_23053207              PQQCEDKFNDLNKRYKRLNDMLGRGTSCQVVENPALLDVIEYLNEKEKDD
Potri.002G068700.1|PACid_27020            PQQCEDKFNDLNKRYKRLNDMLGRGTSCQVVENPALLDVIDYLITEKEKDD
AT1G76870.1                               PQQCEDKFNDLNKRYKKLNEMLGRGTSCEVVENPSLLDKIDYLNEKEKDE
Bradi2g12030.1|PACid_21804939             PQQCEDKFNDLNKRYKRVDLLGRGKACAVVESPALLDAMDELPPRAKEE
SAB18OX LINE SEQ ID NO:6                  PQRCEDKFNDLNKRYKRLTDILGRGTACNVVENHSLLDHMD-ISEKMKED
                                          ** **********:::  :::**  *  .:*  :     : :   *::

GRMZM2G126148_T02|PACid_208616            ARKILSSKHLFYEEMCSYHNNNR---------------
LOC_Os11g06410.1                          ARKILNSKHLFYEEMCSYHNNNR---------------
Sb08g003990.1|PACid_1977601               ARKILSSKHLFYEEMCSYHNNNR---------------
Si010104m|PACid_19697305                  ARKILSSKHLFYEEMCSYHNCNR---------------
AC234952_14.1|PACid_23053207              VRKIINSKHLFYEEMCSYHNCNR---------------
Potri.002G068700.1|PACid_27020            VRKIINSKHLFYEEMCSYHNGNR---------------
AT1G76870.1                               VRRIMSSKHLFYEEMCSYHNGNR---------------
Bradi2g12030.1|PACid_21804939             ARKILSSKHLFFREMCNYHNSPHPHAAAAVTVASHHGAAVHDHEGAAAACF
SAB18OX LINE SEQ ID NO:6                  ARKILNSKHLFYEEMCSYHNNNR---------------
                                          .::::.*****:.***.***                  
```

Figure 1 - con't.

```
GRMZM2G126148_T02|PACid_208616    ------------------------------ANLPEDHALQHSLL-LALRCKEEHD---LRR-ASG
LOC_Os11g06410.1                  ------------------------------ISLPEDPALQQSLQ-LALRCKEDND---FMRHASG
Sb08g003990.1|PACid_1977601       ------------------------------FSLPEDPALQRSLQ-LALKSKDEHD---ARKRASG
Si010104m|PACid_19697305          ------------------------------FSLPEDPALQRSLQ-LALRCKDEHD---TRRRASG
AC234952_14.1|PACid_23053207      ------------------------------LHLPHDPALQRSLQ-IALRNRDDHDNDDVRRSYHD
Potri.002G068700.1|PACid_27020    ------------------------------LHLPHDPALQRSLQ-LALRSRDDHDNDDARRHQHD
AT1G76870.1                       ------------------------------LHLPHDPAVQRSLHLITLGSRDDHDNDEHGKHQNE
Bradi2g12030.1|PACid_21804939     HHPQPVACASSAALHALAPSPAMMNSSTRTEGDEBDDDSENAHPRTSNE
SAB18OX LINE SEQ ID NO:6          ------------------------------ISLPEDPALQQSLQ-LALRCKEDND---FMRHASG
                                                                *: .*   *:. *
                                                                                        : .: *

GRMZM2G126148_T02|PACid_208616    DAD-EDDRSADSDYGE-NDEEQYPVHTRMREPSTTKRKR------HRDVAL
LOC_Os11g06410.1                  DAELDDDQSEDSDYEE-NEEEHRAVDTNIRGPSMHKRMWHVV-DHGDVGF
Sb08g003990.1|PACid_1977601       DAD-EDDQSADTDYEEENDDEHPMVHVNKGTLPMHKRMRYMAADMEDAGF
Si010104m|PACid_19697305          DAD-EDDQSADTDYEEENDDEHPVHVNKGTLPVHKRMRYMA-DQEDVGF
AC234952_14.1|PACid_23053207      DHDEDDHDMETDDHDEFEENYASHGDSRVIFGGLGGTPK---RLRQGQGH
Potri.002G068700.1|PACid_27020    DLDEDDQEIETDDHDEFEENHASHGDCRGIHGVLGGSAK---RPRQGQGH
AT1G76870.1                       DLDDDD-DYEEDHDGALSDRPLKRLRQSQSHEDVGHPNKGYDVPCLPRSQ
Bradi2g12030.1|PACid_21804939     VEEMDEEDVLDDEEEQAPGIKSKHREFHSLNSNGFFPKRRGESSTMEAEE
SAB18OX LINE SEQ ID NO:6          DAELDDDQSEDSDYEE-NEEEHRAVDTNIRGPSMHKRMWHVV-DHGDVGF
                                                           : :

GRMZM2G126148_T02|PACid_208616    VTSNS-HEGSERSD--------PHDVTVDINKAFTDATNMVLLQQD-LAS
LOC_Os11g06410.1                  VTSCS-NDGSGRSD--------PYDV-LDINKPFPDGCDLALVQKD-LAL
Sb08g003990.1|PACid_1977601       GNSSSSHDCSRRSD--------PHSIAVDINKAFPDGTNLALVQKD-LAT
Si010104m|PACid_19697305          GNSSSSHDCSRRSD--------PLSITVDINKVFPDGTNLALVQKD-LAT
AC234952_14.1|PACid_23053207      EDATTFGNSFNCQDYHKSPYPHGQMVQPDGNHALPENMKAAWLQKQWIES
Potri.002G068700.1|PACid_27020    EDAFS--------------------PESSKAVWLQKQWMES
AT1G76870.1                       ADVNRG--------------ISLDSRKAAGLQRQQIES
Bradi2g12030.1|PACid_21804939     DGNNNDNTGAGEGE----APSSAGVQHLQSELAAAAGGDPEQAARRWMRR
SAB18OX LINE SEQ ID NO:6          VTSCS-NDGSGRSD--------PYDV-LDINKPFPDGCDLALVQKD-LAL
                                       :

GRMZM2G126148_T02|PACid_208616    QAIEIQKRRLQIEAKELELTKQRHKWERFRKKDREIERMALENEHMVIE
LOC_Os11g06410.1                  KAAEIQKHRLQIETKAVQLAKQRLKWEMFRKNKDLELEKLALENEQMMLQ
Sb08g003990.1|PACid_1977601       QSAEIEKQRMEIEVEALELAKQRLKWEIFSKKKDRELEKMRLENEQMKME
Si010104m|PACid_19697305          QSAEIEKQRMEIEAEALELAKQRHKWERFSKKKDRELEKMRLENEQMKIE
AC234952_14.1|PACid_23053207      RSVQLEEQKLQIQVEMMELEKQKFKWERFSKKKDRELEKFKLENDRMKIE
Potri.002G068700.1|PACid_27020    RTLQLEERKLQIQQEMLELEKQRFKWQRFSKKRDRELEKLRMENERIKLE
AT1G76870.1                       KSLELEGRKLQIQAEMMELERQQFKWEVFSKRREQKLAKMRMENERMKLE
Bradi2g12030.1|PACid_21804939     RALAVEEQLLACDYREYKLHRQRLKWERFCAGKEREMELAKLRNERARID
                                            :
```

Figure 1 - con't.

| | |
|---|---|
| SAB18OX LINE SEQ ID NO:6 | KAAEIQKHRLQIETKAVQLAKQRLKWEMFRKN------------------- |
| | :: :: : .:* .: .:*: **: *  :: .:  : |
| GRMZM2G126148_T02\|PACid_208616 | NKRLELELRHKELELELKLKGKGNHP---------------------------- |
| LOC_Os11g06410.1 | NKRFELDLRHKELELEIKIKGNANHP---------------------------- |
| Sb08g003990.1\|PACid_1977601 | NRRLELEVRDKELELERKLQGSGSHAMT-------------------------- |
| Si010104m\|PACid_19697305 | NRRLELEVRHKELELELRLKGNRSQAWHDNI----------------------- |
| AC234952_14.1\|PACid_23053207 | NERIALELKRKEIGGTIYSFDGETDEGMVVHDTSASIQGLGGPMTRARTK |
| Potri.002G068700.1\|PACid_27020 | NEQMALELKRKEMGADFN----------------------------------- |
| AT1G76870.1 | NERMSLELKRIELGAKL------------------------------------- |
| Bradi2g12030.1\|PACid_21804939 | GRRMLLMIQHKEIDLAQGLLNRRRGLQQLLLC---------------------- |
| SAB18OX LINE SEQ ID NO:6 | ..:: * :: . *: |

| | |
|---|---|
| GRMZM2G126148_T02\|PACid_208616 | ------------------------------------------------- |
| LOC_Os11g06410.1 | ------------------------------------------------- |
| Sb08g003990.1\|PACid_1977601 | ------------------------------------------------- |
| Si010104m\|PACid_19697305 | ------------------------------------------------- |
| AC234952_14.1\|PACid_23053207 | KAKEALTQLVAKVLESKPTLESMEDKMVMCIKPLEEGWGASLAGCNCVIT |
| Potri.002G068700.1\|PACid_27020 | ------------------------------------------------- |
| AT1G76870.1 | ------------------------------------------------- |
| Bradi2g12030.1\|PACid_21804939 | ------------------------------------------------- |
| SAB18OX LINE SEQ ID NO:6 | ------------------------------------------------- |

| | |
|---|---|
| GRMZM2G126148_T02\|PACid_208616 | ------------------------------- |
| LOC_Os11g06410.1 | ------------------------------- |
| Sb08g003990.1\|PACid_1977601 | ------------------------------- |
| Si010104m\|PACid_19697305 | ------------------------------- |
| AC234952_14.1\|PACid_23053207 | LDRNCVEVVRFLDALLLPYFVVSSVRAVVQQGVL |
| Potri.002G068700.1\|PACid_27020 | ------------------------------- |
| AT1G76870.1 | ------------------------------- |
| Bradi2g12030.1\|PACid_21804939 | ------------------------------- |
| SAB18OX LINE SEQ | ------------------------------- |

Figure 2

SANT domain

Sab18 159-231 (SANT domain) underlined in "Query" SEQ ID NO:6 sequence (highlighted and underlined)-corresponding region in SEQ ID NO:4 is underlined in "Sbjct" sequence Query= SAB18 (SEQ ID NO:6)
Sbjct= SEQ ID NO:4

Score = 518 bits (1333), Expect = 0.0, Method: Compositional matrix adjust.
Identities = 282/442 (64%), Positives = 343/442 (78%), Gaps = 17/442 (4%)

```
Query  49   MEGSNPPGNMTQGPSYGSLDLHGISKQMHPPNSGNQGFNQPQIPGNFTIPMDRVTEPDNI
       108
            MEG+N  P          GSL +   S QMH PN G QGF+  Q+PGN ++ +++ T+ D++
Sbjct  1    MEGNNLPS--------GSL-MRSNSGQMHAPNPGKQGFDHTQMPGNLSMHVNQSTDSDHL
       51

Query  109  SDGVQLGQHGKI-AHHHHHHRHHSKNHGSEEEEHDMNEDAAD---GKDKKGSPWHRMKWT
       164
            S+  Q G+ GK+  HHHHHHR H+KN  S +EEH +NEDA D   GK KKG+ W RMKWT
Sbjct  52   SE-FQFGELGKVDHHHHHHHRQHAKNGMSDDEEHGVNEDATDSQSGKGKKGAAWQRMKWT
       110

Query  165  DSMVKLLITAVSYTGEDPGADLGGGRRNYSMMQKKGKWKAISKVMGERGCHVSPQRCEDK
       224
            DSMVKLLITAVSYTGEDPGAD G G+RN ++MQKKGKWKAISKVMGERGC VSPQ CEDK
Sbjct  111  DSMVKLLITAVSYTGEDPGADSGAGKRNSAIMQKKGKWKAISKVMGERGCSVSPQQCEDK
       170

Query  225  FNDLNKRYKRLTDILGRGTACNVVENHSLLDHM-DISEKMKEDARKILNSKHLFYEEMCS
       283
            FNDLNKRYKRLTDILGRGTAC +VENH+LLD M ++S+KMK+DARKIL+SKHLFYEEMCS
Sbjct  171  FNDLNKRYKRLTDILGRGTACKIVENHALLDCMSNLSDKMKDDARKILSSKHLFYEEMCS
       230

Query  284  YHNNNRISLPEDPALQQSLQLALRCKEDNDFMRHASGDAELDDDQSEDSDYEENEEEHRA
       343
            YHNNNR+SLPEDPALQ+SLQLALRCK+++D R  SGDA+ DD  +    EEN+EE+
Sbjct  231  YHNNNRVSLPEDPALQRSLQLALRCKDEHDLRRGTSGDADEDDQSVDSDSEEENDEENYT
       290
```

Figure 2—con't.

```
Query  344  VDTNIRGPSMHKRMWHVVDHGDVGFVTSCSNDG-SGRSDPYDV-LDINKPFPDGCDLALV
401
            +  +      MHKR+  + D  DVGF  S S+ G S RSD + + LDINK FPDG +LAL
Sbjct  291  LQGDKSALPMHKRLRLMTDQEDVGFGNSSSSHGCSRRSDSHGISLDINKAFPDGTNLALA
350

Query  402  QKDLALKAAEIQKHRLQIETKAVQLAKQRLKWEMFRKN
461
            QKDLA ++A++++ RLQIE +AV LAKQRLKWE F KN
Sbjct  351  QKDLATQSADLEEQRLQIEVQAVYLAKQRLKWERFSKNKDRELEQMRLENEKMRLENKRL
410

Query  462

Sbjct  411  ELEVRHKELELELKQKGSGNHA  432
```

Figure 3
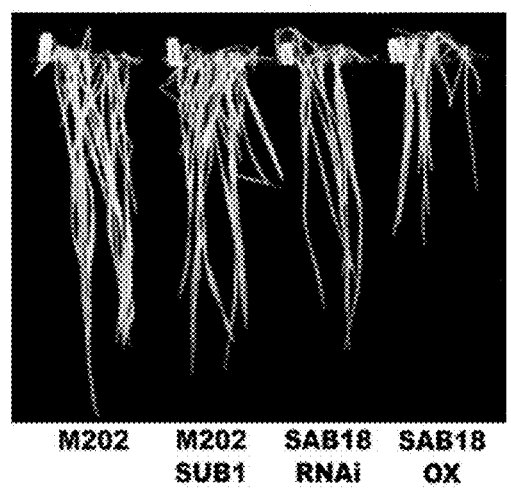
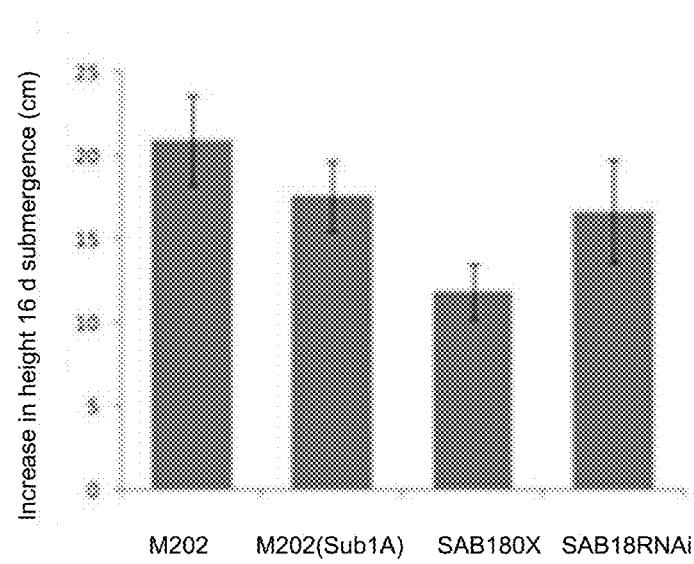

SEQUENCE LISTING

<160> NUMBER OF SEQ ID NOS: 15

<210> SEQ ID NO 1
<211> LENGTH: 1452
<212> TYPE: DNA
<213> ORGANISM: Oryza sativa

<400> SEQUENCE: 1
atgtctatcc tcctttggct atcccatgta ctgctgaaac ttcattactt gaggttatat    60
tcatgtgcat cctcgtgcac tcctgtgtcc atcttatatg gtaccaacaa gaagttgaag   120

```
tgtttgggtg atcgctttgg ggaaatggaa ggcagcaacc cacctggtaa tatgacacag     180
ggaccttcct atgggagttt agatttgcat ggtatctcca agcaaatgca tcctccaaac     240
tcaggaaatc agggcttcaa ccagcctcag ataccaggga attttaccat tcctatggat     300
agggttacag agcctgataa catctctgat ggagttcagt taggacaaca tgggaagatt     360
gcccatcatc accatcacca cagacaccac tcaaagaacc atgggagtga ggaagaggag     420
cacgatatga atgaggatgc tgctgatggc aaagacaaga agggctctcc atggcatcgg     480
atgaagtgga cagattcaat ggtgaagctt ttgattactg cagtatccta cacaggggag     540
gatcctggag ctgatttagg cggtgggagg aggaactatt caatgatgca aagaagggaa     600
aaatggaaag caatatcaaa ggtcatgggc gagagaggtt gccatgtgtc gccacagcgg     660
tgtgaggata agttcaatga ccttaataag agatacaaaa gactaacaga tatccttgga     720
aggggtactg cttgtaatgt tgtggagaat cactcacttc ttgatcacat ggatatttct     780
gagaagatga agaggatgca aggaagata ctgaactcca aacacttgtt ctatgaagag     840
atgtgttcct accataataa taaccgtata agtctgcctg aagatcccgc acttcagcag     900
tcactacagc ttgctcttag atgtaaagag ataatgatt tcatgaggca tgcaagtgga     960
gatgctgaac tagatgatga tcagagtgaa gattcagatt atgaggagaa tgaggaagaa    1020
catcgagcag ttgataccaa tataaggggc ccctcaatgc ataaaaggat gtggcatgtt    1080
gtagatcatg tgatgtaggg ttttgtcacc tcatgctcga atgatggtag tgggaggtct    1140
gatccctatg acgtgttgga tatcaacaaa cccttccag atggatgtga tttggctttg     1200
gtgcaaaaag acttggctct gaaagcagca gagattcaaa acatcgtttt gcagattgaa    1260
accaaggctg tgcaactcgc aaagcaacgt ctcaagtggg agatgttcag gaagaactag    1320
gacttggaat tggaaaagtt ggcgttggag aatgaacaaa tgatgcttca gaataagcgg    1380
tttgagcttg acctaagaca caaggagcta gaacttgaga ttaagataaa gggcaatgct    1440
aatcatccat ga                                                       1452
```

<210> SEQ ID NO 2
<211> LENGTH: 483
<212> TYPE: PRT
<213> ORGANISM: Oryza sativa
<220> FEATURE:
<221> NAME/KEY: MISC_FEATURE
<222> LOCATION: (159)..(231)
<223> OTHER INFORMATION: SANT domain

<400> SEQUENCE: 2

```
Met Ser Ile Leu Leu Trp Leu Ser His Val Leu Leu Lys Leu His Tyr
1               5                   10                  15

Leu Arg Leu Tyr Ser Cys Ala Ser Ser Cys Thr Pro Val Ser Ile Leu
            20                  25                  30

Tyr Gly Thr Asn Lys Lys Leu Lys Cys Leu Gly Asp Arg Phe Gly Glu
        35                  40                  45

Met Glu Gly Ser Asn Pro Pro Gly Asn Met Thr Gln Gly Pro Ser Tyr
    50                  55                  60

Gly Ser Leu Asp Leu His Gly Ile Ser Lys Gln Met His Pro Asn
65                  70                  75                  80

Ser Gly Asn Gln Gly Phe Asn Gln Pro Gln Ile Pro Gly Asn Phe Thr
                85                  90                  95

Ile Pro Met Asp Arg Val Thr Glu Pro Asp Asn Ile Ser Asp Gly Val
            100                 105                 110
```

-continued

```
Gln Leu Gly Gln His Gly Lys Ile Ala His His His His His Arg
            115                 120                 125
His His Ser Lys Asn His Gly Ser Asp Glu Glu His Asp Met Asn
        130                 135                 140
Glu Asp Ala Ala Asp Gly Lys Asp Lys Lys Gly Ser Pro Trp His Arg
145                 150                 155                 160
Met Lys Trp Thr Asp Ser Met Val Lys Leu Leu Ile Thr Ala Val Ser
                165                 170                 175
Tyr Thr Gly Glu Asp Pro Gly Ala Asp Leu Gly Gly Gly Arg Arg Asn
            180                 185                 190
Tyr Ser Met Met Gln Lys Lys Gly Lys Trp Lys Ala Ile Ser Lys Val
        195                 200                 205
Met Gly Glu Arg Gly Cys His Val Ser Pro Gln Gln Cys Glu Asp Lys
210                 215                 220
Phe Asn Asp Leu Asn Lys Arg Tyr Lys Arg Leu Thr Asp Ile Leu Gly
225                 230                 235                 240
Arg Gly Thr Ala Cys Asn Val Val Glu Asn His Ser Leu Leu Asp His
                245                 250                 255
Met Asp Ile Ser Glu Lys Met Lys Glu Asp Ala Arg Lys Ile Leu Asn
            260                 265                 270
Ser Lys His Leu Phe Tyr Glu Glu Met Cys Ser Tyr His Asn Asn Asn
        275                 280                 285
Arg Ile Ser Leu Pro Glu Asp Pro Ala Leu Gln Gln Ser Leu Gln Leu
    290                 295                 300
Ala Leu Arg Cys Lys Glu Asp Asn Asp Phe Met Arg His Ala Ser Gly
305                 310                 315                 320
Asp Ala Glu Leu Asp Asp Gln Ser Glu Asp Ser Asp Tyr Glu Glu
                325                 330                 335
Asn Glu Glu Glu His Arg Ala Val Asp Thr Asn Ile Arg Gly Pro Ser
            340                 345                 350
Met His Lys Arg Met Trp His Val Val Asp His Gly Asp Val Gly Phe
        355                 360                 365
Val Thr Ser Cys Ser Asn Asp Gly Ser Gly Arg Ser Asp Pro Tyr Asp
370                 375                 380
Val Leu Asp Ile Asn Lys Pro Phe Pro Asp Gly Cys Asp Leu Ala Leu
385                 390                 395                 400
Val Gln Lys Asp Leu Ala Leu Lys Ala Ala Glu Ile Gln Lys His Arg
                405                 410                 415
Leu Gln Ile Glu Thr Lys Ala Val Gln Leu Ala Lys Gln Arg Leu Lys
            420                 425                 430
Trp Glu Met Phe Arg Lys Asn Lys Asp Leu Glu Leu Glu Lys Leu Ala
        435                 440                 445
Leu Glu Asn Glu Gln Met Met Leu Gln Asn Lys Arg Phe Glu Leu Asp
    450                 455                 460
Leu Arg His Lys Glu Leu Glu Leu Glu Ile Lys Ile Lys Gly Asn Ala
465                 470                 475                 480
Asn His Pro

<210> SEQ ID NO 3
<211> LENGTH: 4811
<212> TYPE: DNA
<213> ORGANISM: Oryza sativa

<400> SEQUENCE: 3
```

```
gttcagcttt ggcattttct tctgagaaag agaaacctcg tgctcggcga ggcccaatat      60
ttcggcggag gctgaggcgg aggcggaggc ggattgtctc ctcgccggcg ttcagttcag     120
tcgccggata ccgtcgtgag tcagctctcc ttttccctcc cgatgcatcg ctttgttggt     180
cgcagcggct tccgctgtca tcgcgtgggg gcgttaaacc caatgagttt tttgtgtgtg     240
cgtgtgtgtg tgtgtgtggg ggggggggg tactcgccgc tcggatcgct ggcgacgagc      300
actccgcgta ggctcgtcgc ggccacgtac gccatcccga gctcggggc taccccggtc      360 ggaggcggag cgcttggggg ccggggttta atcgtgcgga ggactcggta gggctcgcca     420
tacctcgcgc cgtccggcgg cgcagagcgc ggcgtcgccg ctggggagaa ggacggactc     480
aacgagacga gcgagcgacg gccgacaggc gaaggcgttc tcgcttcttg gcctctcgcc     540
gttgaattgg agacccacat tgggcttgtt ttgtgtgtta ctagcatcac caagagttcc     600
cctactactc ccaatttcaa attttggggt ttttcgagca aaaaaatgg atccaacaga      660 tatccaaacc agcttccaaa aattttgaga ccctaatccc gtgtttccgt tctccaccag     720
tagagaatac ctcccgctcc caatccactg cagccgggca gttttcgcgc gctgccgagg     780
tgcttggttc ccccatctcc attgattccc catctcgtgc gattggcgga gctgatgagt     840
gacgacagcc acgggcgagc gggaggtggc acgtcgacag gcggcggagg gccgccagcg     900
cagctgcggc agccggcaag ggcggctggg tgggctgcag gctgtggctg cagttgggca     960
gcgcggcagt agcaggtggc gggccaacaa gtagcagggc aggccggcag cagcagcaga    1020
tcaacaggat gattcaatct ttgctatttg ccttatccac cttaaagata gcctattaat    1080
cgatccatct ttgctaggag tatctgtttt gcagattatt tatatgtcta tcctcctttg    1140
gctatcccat gtactgctga aacttcatta cttgaggtaa ttttagtgt catgaggggt     1200 tgttgtcatg cttaatatag acttgttaag ataatattgt gtggtacaat gtggtgcaat    1260
ttgagaattt ttttcccatt attcttgggt tgattctcat gataattcat gagccacacc    1320
tcttcttttt ttagtcctct gccactgatc gtgcgtgtga aatttgata gtttatattt     1380 tggtgtggtt cgtggattat tattacacat ggacagctaa tttgcgcacg acactttgtt    1440
tttactattt tttcttgtga ggtgacaaat tgatttattt ttccccatgc attttcttct    1500
cgttagttat gagtagcatg gaaaggttgc aacattttt tgttttggct agtggttgat     1560
tggttgccac ttgccactgc aataatgttt taaaattgtt ccactcacat tacccagtgg    1620
agtaatatgg tttgatttgt catttgtgct gctgattaat taggttgttg gttgatgcag    1680
tttagattct tcagaacact ctgattttta gtgctccaat attatcttgc tttggcaatt    1740
atgacaacta taggaggctg aaattaccct ttattgtgta acactgatt aaaatctctt     1800 caaatttgtg cattagttat ttcttattag gtggccctga ttacatatgg actctagtta    1860
agatatattg tgtgattctg aagatctttt tcttttagca aattgattct gaagattgag    1920
atgtatagaa atgtgcaata tacatgtgtt ggatttccaa aaattcatac caaactgcca    1980
tttcaggtta tattcatgtg catcctcgtg cactcctgtg tccatcttat atggtaccaa    2040
caagaagttg aagtgtttgg gtgatcgctt tggggaaatg gaaggcagca acccacctgg    2100
taatatgaca cagggacctt cctatgggag tttagatttg catggtatct ccaagcaaat    2160
gcatcctcca aactcaggaa atcagggctt caaccagcct cagataccag ggaatttac     2220 cattcctatg gatagggtta cagagcctga taacatctct gatggagttc agttaggaca    2280
acatgggaag attgccccatc atcaccatca ccacagacac cactcaaaga accatggag    2340 tgatgaagag gagcacgata tgaatgagga tgctgctgat ggcaaagaca agaagggctc    2400
```

```
tccatggcat cggatgaagt ggacagattc aatggtgaag cttttgatta ctgcagtatc    2460
ctacacaggg gaggatcctg gagctgattt aggcggtggg aggaggaact attcaatgat    2520
gcaaaagaag ggaaaatgga aagcaatatc aaaggtcatg ggcgagagag gttgccatgt    2580
gtcgccacag cagtgtgagg ataagttcaa tgaccttaat aagagataca aaagactaac    2640
agatatcctt ggaaggggta ctgcttgtaa tgttgtggag aatcactcac ttcttgatca    2700
catggatatt tctgagaaga tgaaagagga tgcaaggaag atactgaact ccaaacactt    2760
gttctatgaa gagatgtgtt cctaccataa taataaccgt ataagtctgc ctgaagatcc    2820
cgcacttcag cagtcactac agcttgctct tagatgtaaa gaggataatg atttcatgag    2880
gcatgcaagt ggagatgctg aactagatga tgatcagagt gaagattcag attatgagga    2940
gaatgaggaa gaacatcgag cagttgatac caatataagg ggcccctcaa tgcataaaag    3000
gatgtggcat gttgtagatc atggtgatgt aggttttgtc acctcatgct cgaatgatgg    3060
tagtgggagg tctgatccct atgacgtgtt ggatatcaac aaaccctttc cagatggatg    3120
tgatttggct ttggtgcaaa aagacttggc tctgaaagca gcagagattc aaaaacatcg    3180
tttgcagatt gaaaccaagg ctgtgcaact cgcaaagcaa cgtctcaagt gggagatgtt    3240
caggaagaac aaggacttgg aattggaaaa gttggcgttg gagaatgaac aaatgatgct    3300
tcagaataag cggtttgagc ttgacctaag acacaaggag ctagaacttg agattaagat    3360
aaagggcaat gctaatcatc catgatcttt gttctgttag cacttcattt cgcaatatgg    3420
taagcaaatg gactagattt tcagttactt ttactaaaaa atgctcaatg tttataattt    3480
gggtagcttc ttgtgggagt tttttcatga caagttttta ggtagtactg tgctactagt    3540
gtatatggaa ctatggaaat catgcattgg ggctgtttcc tattgatagt gtttacttca    3600
gctttatagt cccaaacccc tgtagtacaa aaattagtcc catccataga tagaggcggc    3660
atcagttttt gacggagatt ttactgttct acagcaaaga aggcatcagt tagatatgta    3720
ctatcaactg ggagttattt cgtgactagt attaagatca actgcaatga ctgtggttct    3780
atacatggtg tacttgggtg taaacataat cagcgaataa aagataacaa aagggaagca    3840
actgcatcac caagatacaa atagtgatgc tgctcggatt tggtgatctt gtgtgctgtc    3900
agattggcac ttccaagctg agtttcaata tccaataatc ttcatgattc aaagtcaaca    3960
atatccaaat ttttctttt cccctgatta aacagatatt agttcttact cttgtatgga    4020
taagttgtta atgggtaatt ggtatggtgt ttgttatctt gacaagaagt agcttatatt    4080
tgttcaattg cacgaacaat gtttacagtt tgtctgtatg tagaacactg cttttaaata    4140
tgatggtatg ctttattaca gagagtttac tctaaaactc gtaagtatat aactgatgag    4200
tctagcttag ctggttcacc tatgcttagc caactccatc gtttgctctt tagcttatca    4260
accacagcca aaatttgaat tttaaatctt aaatttatgg ctaattttag cgaaaatatg    4320
tgacttaact ctgaacgttt gcctctaaaa cagattacat tgtttatagtt ttttctaaaa    4380 tggattgcag atggttatca gggtagcatc ctgttatttt ctgcattgag ttttgtttct    4440
tccatgctct tccaataatt ccaagttctc tctagaactg aataatggtt gtctgaaact    4500
caattcgttc cccggattgt taatttcagg ttgcagatca attcaattca ggaccgtgtt    4560
tatgcaagat ggtagaggtg gcagattgtt tatgcaagat ggtagaggtg gcagattatc    4620
tgtgactact gacaagtgac aacaatttca atgctttata gctagctcag tgatcctctc    4680
ctcttgttgt ttatatatca ttatatctcc tgattctctc tacttgtaaa atttccatgt    4740
```

-continued

```
gatactgggc tccatctgta ttctaaagtt ttcatcattt ttttctatcc aactttgttt    4800
tactcaatca a                                                          4811
```

<210> SEQ ID NO 4
<211> LENGTH: 432
<212> TYPE: PRT
<213> ORGANISM: Oryza sativa
<220> FEATURE:
<221> NAME/KEY: MISC_FEATURE
<222> LOCATION: (105)..(177)
<223> OTHER INFORMATION: SANT domain

<400> SEQUENCE: 4

```
Met Glu Gly Asn Asn Leu Pro Ser Gly Ser Leu Met Arg Ser Asn Ser
1               5                   10                  15

Gly Gln Met His Ala Pro Asn Pro Gly Lys Gln Gly Phe Asp His Thr
            20                  25                  30

Gln Met Pro Gly Asn Leu Ser Met His Val Asn Gln Ser Thr Asp Ser
        35                  40                  45

Asp His Leu Ser Glu Phe Gln Phe Gly Glu Leu Gly Lys Val Asp His
    50                  55                  60

His His His His His Arg Gln His Ala Lys Asn Gly Met Ser Asp
65                  70                  75                  80

Asp Glu Glu His Gly Val Asn Glu Asp Ala Thr Asp Ser Gln Ser Gly
                85                  90                  95

Lys Gly Lys Lys Gly Ala Ala Trp Gln Arg Met Lys Trp Thr Asp Ser
            100                 105                 110

Met Val Lys Leu Leu Ile Thr Ala Val Ser Tyr Thr Gly Glu Asp Pro
        115                 120                 125

Gly Ala Asp Ser Gly Ala Gly Lys Arg Asn Ser Ala Ile Met Gln Lys
    130                 135                 140

Lys Gly Lys Trp Lys Ala Ile Ser Lys Val Met Gly Glu Arg Gly Cys
145                 150                 155                 160

Ser Val Ser Pro Gln Gln Cys Glu Asp Lys Phe Asn Asp Leu Asn Lys
                165                 170                 175

Arg Tyr Lys Arg Leu Thr Asp Ile Leu Gly Arg Gly Thr Ala Cys Lys
            180                 185                 190

Ile Val Glu Asn His Ala Leu Leu Asp Cys Met Ser Asn Leu Ser Asp
        195                 200                 205

Lys Met Lys Asp Asp Ala Arg Lys Ile Leu Ser Ser Lys His Leu Phe
    210                 215                 220

Tyr Glu Glu Met Cys Ser Tyr His Asn Asn Asn Arg Val Ser Leu Pro
225                 230                 235                 240

Glu Asp Pro Ala Leu Gln Arg Ser Leu Gln Leu Ala Leu Arg Cys Lys
                245                 250                 255

Asp Glu His Asp Leu Arg Arg Gly Thr Ser Gly Asp Ala Asp Glu Asp
            260                 265                 270

Asp Gln Ser Val Asp Ser Asp Ser Glu Glu Asn Asp Glu Asn
        275                 280                 285

Tyr Thr Leu Gln Gly Asp Lys Ser Ala Leu Pro Met His Lys Arg Leu
    290                 295                 300

Arg Leu Met Thr Asp Gln Glu Asp Val Gly Phe Gly Asn Ser Ser Ser
305                 310                 315                 320

Ser His Gly Cys Ser Arg Arg Ser Asp Ser His Gly Ile Ser Leu Asp
                325                 330                 335
```

```
Ile Asn Lys Ala Phe Pro Asp Gly Thr Asn Leu Ala Leu Ala Gln Lys
                340                 345                 350

Asp Leu Ala Thr Gln Ser Ala Asp Leu Glu Glu Gln Arg Leu Gln Ile
                355                 360                 365

Glu Val Gln Ala Val Tyr Leu Ala Lys Gln Arg Leu Lys Trp Glu Arg
            370                 375                 380

Phe Ser Lys Asn Lys Asp Arg Glu Leu Glu Gln Met Arg Leu Glu Asn
385                 390                 395                 400

Glu Lys Met Arg Leu Glu Asn Lys Arg Leu Glu Leu Val Arg His
                405                 410                 415

Lys Glu Leu Glu Leu Glu Leu Lys Gln Lys Gly Ser Gly Asn His Ala
                420                 425                 430

<210> SEQ ID NO 5
<211> LENGTH: 649
<212> TYPE: PRT
<213> ORGANISM: Oryza sativa

<400> SEQUENCE: 5

Met Ser Asn Thr Tyr Thr Arg Trp Ile His His Gly Glu Pro Leu Val
1               5                   10                  15

Met Val Thr Gly Asn Val Glu His Leu Asn Glu Asp Ile Gly Cys Asn
                20                  25                  30

Val Glu His Leu Asn Glu Asp Val Ser Cys Asn Val Glu Phe Glu Thr
            35                  40                  45

Asn Glu Pro Pro Asp Asp Pro Glu Asp Gln Met Tyr Arg Met Val
    50                  55                  60

Gln Asp Leu Tyr Pro Asp Gln Asn His Gly Pro Arg Thr Lys Ser Lys
65                  70                  75                  80

Phe Ala Thr Ile Leu Glu Glu Met Lys Gln Val Leu His Pro Gly Gly
                85                  90                  95

Pro Tyr Thr Arg Phe Ser Phe Val Val Lys Leu Leu His Ile Lys Ser
                100                 105                 110

Phe Tyr Arg Ile Ser Asn Val Ala Phe Ser Ala Phe Leu Asp Leu Leu
            115                 120                 125

Ser Ser Ala Phe Pro Asn Cys Ser Leu Pro Ala Ser Tyr Ala Glu Ala
    130                 135                 140

Lys Thr Phe Ile Arg Ala Leu Gly Leu Gly Tyr Glu Ser Ile His Val
145                 150                 155                 160

Cys Pro Asn Asn Cys Val Leu Phe Arg Lys Glu Leu Ala Lys Lys Asp
                165                 170                 175

Ala Cys Pro Ile Cys Gly Ala Ser Arg Trp Lys Asp Ala Asp Ser Arg
            180                 185                 190

Arg Lys Ile Pro Glu Lys Val Leu Arg His Phe Pro Leu Ile Pro Arg
        195                 200                 205

Leu Lys Arg Met Phe Gly Ser Lys Glu Leu Ser Ala Glu Ala Gln Trp
    210                 215                 220

His Lys Leu Lys Arg Lys Pro Val Asp Asn Glu Leu Ser His Pro Ala
225                 230                 235                 240

Asp Gly Glu Ala Trp Lys Asp Phe Asp Arg Lys Tyr Gly Trp Phe Ala
                245                 250                 255

Asn Asp Ala Arg Asn Val Arg Leu Gly Leu Ala Thr Asp Gly Phe Asn
            260                 265                 270

Pro Phe Gly Lys Met Ser Ser Ser Tyr Ser Met Trp Pro Val Phe Leu
        275                 280                 285
```

```
Ile Pro Tyr Asn Phe Pro Pro Trp Gln Cys Met Glu Gln Ser Asn Phe
    290                 295                 300
Met Met Cys Leu Leu Ile Pro Gly Pro Thr Cys Pro Gly Lys Asp Met
305                 310                 315                 320
Asp Leu Phe Leu Gln Pro Leu Val Glu Glu Leu Leu Asn Leu Trp Ser
                325                 330                 335
Gly Val Pro Thr Leu Asp Ala Leu Thr Gly Lys Glu Phe Asp Leu His
            340                 345                 350
Ala Ala Ile Ile Trp Cys Ile His Asp Tyr Pro Ala Leu Ser Thr Leu
        355                 360                 365
Ser Gly Arg Val Thr Arg Gly Tyr Tyr Ala Cys Val Cys Cys Asp Lys
    370                 375                 380
Asn Pro Cys Tyr Lys Arg Leu Arg Asn Lys Ile Cys Tyr Ile Gly His
385                 390                 395                 400
Arg Arg Phe Leu Pro Val Asp His Ile Trp Arg Arg Lys Lys Asp Phe
                405                 410                 415
Asn Gly Gln Thr Glu Glu Arg Ala Gln Pro Glu Glu Phe Thr Gln Asp
            420                 425                 430
Glu Leu Met Gln Gln Leu Ala Arg Val Glu His Val Arg Pro Gly Asn
        435                 440                 445
His Pro Asn Asn Lys Lys Arg Lys Val Glu Glu Gly Gln Cys Trp
    450                 455                 460
Lys Arg Arg Ser Thr Leu Trp Asp Leu Pro Tyr Trp Ser Asn Leu Lys
465                 470                 475                 480
Leu Arg His Asn Leu Asp Val Met His Ile Glu Lys Asn Ile Cys Glu
                485                 490                 495
Ala Leu Leu Gly Thr Phe Leu Asp Ile Ala Gly Lys Ser Lys Asp Ser
            500                 505                 510
Val Thr Ala Arg Leu Asp Leu Glu Asp Met Gly Ile Arg Lys Asn Leu
        515                 520                 525
His Leu Lys Asp Asp Gly Asn Ser Thr Cys Thr Ala Leu His Ala Pro
    530                 535                 540
Tyr Val Met Thr Lys Ala Gln Arg Lys Ala Phe Cys Ala Phe Ile Lys
545                 550                 555                 560
Asn Val Lys Phe Pro Asp Gly Tyr Ala Ser Asn Leu Ala Arg Cys Val
                565                 570                 575
Ser Val Asp Glu Cys Lys Val Gln Ala Leu Lys Thr His Asp Cys His
            580                 585                 590
Ile Leu Leu Gln Arg Ile Leu Pro Ala Gly Leu Arg Gly Ile Met His
        595                 600                 605
Lys Glu Ile Tyr Glu Thr Ile Ala Glu Leu Gly Asn Phe Phe Gln Gln
    610                 615                 620
Ile Cys Ala Lys Lys Leu Lys Leu Asp Ala Leu Asn Lys Met Arg Gly
625                 630                 635                 640
Glu Ile Pro Ile Ile Leu Cys Lys Leu
                645
```

<210> SEQ ID NO 6
<211> LENGTH: 439
<212> TYPE: PRT
<213> ORGANISM: Oryza sativa
<220> FEATURE:
<221> NAME/KEY: MISC_FEATURE
<222> LOCATION: (159)..(234)
<223> OTHER INFORMATION: SANT domain

<400> SEQUENCE: 6

```
Met Ser Ile Leu Leu Trp Leu Ser His Val Leu Leu Lys Leu His Tyr
1               5                   10                  15

Leu Arg Leu Tyr Ser Cys Ala Ser Ser Cys Thr Pro Val Ser Ile Leu
            20                  25                  30

Tyr Gly Thr Asn Lys Lys Leu Lys Cys Leu Gly Asp Arg Phe Gly Glu
            35                  40                  45

Met Glu Gly Ser Asn Pro Gly Asn Met Thr Gln Gly Pro Ser Tyr
50                  55                  60

Gly Ser Leu Asp Leu His Gly Ile Ser Lys Gln Met His Pro Asn
65                  70                  75                  80

Ser Gly Asn Gln Gly Phe Asn Gln Pro Gln Ile Pro Gly Asn Phe Thr
                85                  90                  95

Ile Pro Met Asp Arg Val Thr Glu Pro Asp Asn Ile Ser Asp Gly Val
                100                 105                 110

Gln Leu Gly Gln His Gly Lys Ile Ala His His His His His His Arg
            115                 120                 125

His His Ser Lys Asn His Gly Ser Glu Glu Glu His Asp Met Asn
130                 135                 140

Glu Asp Ala Ala Asp Gly Lys Asp Lys Lys Gly Ser Pro Trp His Arg
145                 150                 155                 160

Met Lys Trp Thr Asp Ser Met Val Lys Leu Leu Ile Thr Ala Val Ser
                165                 170                 175

Tyr Thr Gly Glu Asp Pro Gly Ala Asp Leu Gly Gly Arg Arg Asn
            180                 185                 190

Tyr Ser Met Met Gln Lys Lys Gly Lys Trp Lys Ala Ile Ser Lys Val
            195                 200                 205

Met Gly Glu Arg Gly Cys His Val Ser Pro Gln Arg Cys Glu Asp Lys
210                 215                 220

Phe Asn Asp Leu Asn Lys Arg Tyr Lys Arg Leu Thr Asp Ile Leu Gly
225                 230                 235                 240

Arg Gly Thr Ala Cys Asn Val Val Glu Asn His Ser Leu Leu Asp His
                245                 250                 255

Met Asp Ile Ser Glu Lys Met Lys Glu Asp Ala Arg Lys Ile Leu Asn
                260                 265                 270

Ser Lys His Leu Phe Tyr Glu Glu Met Cys Ser Tyr His Asn Asn Asn
            275                 280                 285

Arg Ile Ser Leu Pro Glu Asp Pro Ala Leu Gln Gln Ser Leu Gln Leu
290                 295                 300

Ala Leu Arg Cys Lys Glu Asp Asn Asp Phe Met Arg His Ala Ser Gly
305                 310                 315                 320

Asp Ala Glu Leu Asp Asp Asp Gln Ser Glu Asp Ser Asp Tyr Glu Glu
                325                 330                 335

Asn Glu Glu Glu His Arg Ala Val Asp Thr Asn Ile Arg Gly Pro Ser
            340                 345                 350

Met His Lys Arg Met Trp His Val Val Asp His Gly Asp Val Gly Phe
            355                 360                 365

Val Thr Ser Cys Ser Asn Asp Gly Ser Gly Arg Ser Asp Pro Tyr Asp
            370                 375                 380

Val Leu Asp Ile Asn Lys Pro Phe Pro Asp Gly Cys Asp Leu Ala Leu
385                 390                 395                 400

Val Gln Lys Asp Leu Ala Leu Lys Ala Ala Glu Ile Gln Lys His Arg
```

```
              405                 410                 415
Leu Gln Ile Glu Thr Lys Ala Val Gln Leu Ala Lys Gln Arg Leu Lys
            420                 425                 430

Trp Glu Met Phe Arg Lys Asn
        435

<210> SEQ ID NO 7
<211> LENGTH: 1452
<212> TYPE: DNA
<213> ORGANISM: Oryza sativa

<400> SEQUENCE: 7
atgtctatcc tcctttggct atcccatgta ctgctgaaac ttcattactt gaggttatat      60
tcatgtgcat cctcgtgcac tcctgtgtcc atcttatatg gtaccaacaa gaagttgaag     120
tgtttgggtg atcgctttgg ggaaatggaa ggcagcaacc cacctggtaa tatgacacag     180
ggaccttcct atgggagttt agatttgcat ggtatctcca agcaaatgca tcctccaaac     240
tcaggaaatc agggcttcaa ccagcctcag ataccaggga attttaccat tcctatggat     300
agggttacag agcctgataa catctctgat ggagttcagt taggacaaca tgggaagatt     360
gcccatcatc accatcacca cagacaccac tcaaagaacc atgggagtga ggaagaggag     420
cacgatatga atgaggatgc tgctgatggc aaagacaaga agggctctcc atggcatcgg     480
atgaagtgga cagattcaat ggtgaagctt ttgattactg cagtatccta cagggggag      540 gatcctggag ctgatttagg cggtgggagg aggaactatt caatgatgca aagaaggga      600 aaatggaaag caatatcaaa ggtcatgggc gagagaggtt gccatgtgtc gccacagcgg     660
tgtgaggata agttcaatga ccttaataag agatacaaaa gactaacaga tatccttgga     720
aggggtactg cttgtaatgt tgtggagaat cactcacttc ttgatcacat ggatattttct    780 gagaagatga agaggatgc aaggaagata ctgaactcca aacacttgtt ctatgaagag      840
atgtgttcct accataataa taaccgtata agtctgcctg aagatcccgc acttcagcag     900
tcactacagc ttgctcttag atgtaaagag gataatgatt tcatgaggca tgcaagtgga     960
gatgctgaac tagatgatga tcagagtgaa gattcagatt atgaggagaa tgaggaagaa    1020
catcgagcag ttgataccaa tataaggggc ccctcaatgc ataaaaggat gtggcatgtt    1080
gtagatcatg gtgatgtagg ttttgtcacc tcatgctcga atgatggtag tgggaggtct    1140
gatccctatg acgtgttgga tatcaacaaa cccttccag atggatgtga tttggctttg     1200
gtgcaaaaag acttggctct gaaagcagca gagattcaaa acatcgtttt gcagattgaa    1260
accaaggctg tgcaactcgc aaagcaacgt ctcaagtggg agatgttcag gaagaactag    1320
gacttggaat tggaaaagtt ggcgttggag aatgaacaaa tgatgcttca gaataagcgg    1380
tttgagcttg acctaagaca caaggagcta gaacttgaga ttaagataaa gggcaatgct    1440
aatcatccat ga                                                       1452

<210> SEQ ID NO 8
<211> LENGTH: 436
<212> TYPE: PRT
<213> ORGANISM: Zea mays

<400> SEQUENCE: 8

Met Glu Gly Asn Asp Leu Pro Pro Gly Asn Met Leu Gln Gly Ala Pro
1               5                   10                  15

Tyr Asp Ser Leu Asp Leu His Gly Asp Ser Met Ala Lys His Ala Pro
            20                  25                  30
```

```
Asn Ser Gly Lys Gln Ile Phe Ser Ser Gln Met Pro Gly Thr Phe
         35                  40                  45

Thr Met Ser Met Thr Arg Ala Thr Glu Pro Asp Asp Phe Pro Gly Phe
 50                  55                  60

Gln Phe Lys Glu His Gly Lys Ser Asp Asp His His His Gln Tyr
 65                  70                  75                  80

His Ser His His Gln Lys Asn Cys Met Ser Asp Gly Glu His Asp
             85                  90                  95

Met Ala Glu Asp Ala Thr Asp Thr Pro Ser Gly Lys Gly Lys Lys Gly
             100                 105                 110

Ser Ala Trp His Arg Met Lys Trp Thr Asp Ser Met Val Lys Leu Leu
             115                 120                 125

Ile Thr Ala Val Ser Tyr Thr Gly Asp Asp His Gly Ala Asp Ser Gly
 130                 135                 140

Gly Gly Arg Arg Asn Ile Ala Ile Thr Gln Lys Gly Lys Trp Lys
145                 150                 155                 160

Ala Ile Ser Lys Val Met Gly Glu Arg Gly Cys His Val Ser Pro Gln
             165                 170                 175

Gln Cys Glu Asp Lys Phe Asn Asp Leu Asn Lys Arg Tyr Lys Arg Leu
             180                 185                 190

Ile Asp Ile Leu Gly Met Gly Thr Ala Cys Asn Val Val Ala Asn Pro
             195                 200                 205

Ala Leu Leu Asp Ser Met Asn His Leu Ser Asp Lys Met Lys Asp Asn
 210                 215                 220

Ala Lys Lys Ile Leu Ser Ser Lys His Leu Phe Tyr Glu Glu Met Cys
225                 230                 235                 240

Ser Tyr His Asn Asn Arg Ala Asn Leu Pro Glu Asp His Ala Leu
             245                 250                 255

Gln His Ser Leu Leu Leu Ala Leu Arg Cys Lys Glu Glu His Asp Leu
             260                 265                 270

Arg Arg Ala Ser Gly Asp Ala Asp Glu Asp Asp Arg Ser Ala Asp Ser
 275                 280                 285

Asp Tyr Gly Glu Asn Asp Glu Glu Gln Tyr Pro Val His Thr Arg Met
 290                 295                 300

Arg Glu Pro Ser Thr Thr Lys Arg Lys Arg His Arg Asp Val Ala Leu
305                 310                 315                 320

Val Thr Ser Asn Ser His Glu Gly Ser Glu Arg Ser Asp Pro His Asp
             325                 330                 335

Val Thr Val Asp Ile Asn Lys Ala Phe Thr Asp Ala Thr Asn Met Val
             340                 345                 350

Leu Leu Gln Gln Asp Leu Ala Ser Gln Ala Ile Glu Ile Gln Lys Arg
             355                 360                 365

Arg Leu Gln Ile Glu Ala Lys Glu Leu Glu Leu Thr Lys Gln Arg His
 370                 375                 380

Lys Trp Glu Arg Phe Arg Lys Lys Asp Arg Glu Ile Glu Arg Met
385                 390                 395                 400

Ala Leu Glu Asn Glu His Met Val Ile Glu Asn Lys Arg Leu Glu Leu
             405                 410                 415

Glu Leu Arg His Lys Glu Leu Glu Leu Glu Leu Lys Leu Lys Gly Lys
             420                 425                 430

Gly Asn His Pro
             435
```

<210> SEQ ID NO 9
<211> LENGTH: 483
<212> TYPE: PRT
<213> ORGANISM: Oryza sativa

<400> SEQUENCE: 9

Met Ser Ile Leu Leu Trp Leu Ser His Val Leu Leu Lys Leu His Tyr
1               5                   10                  15

Leu Arg Leu Tyr Ser Cys Ala Ser Ser Cys Thr Pro Val Ser Ile Leu
            20                  25                  30

Tyr Gly Thr Asn Lys Lys Leu Lys Cys Leu Gly Asp Arg Phe Gly Glu
        35                  40                  45

Met Glu Gly Ser Asn Pro Pro Gly Asn Met Thr Gln Gly Pro Ser Tyr
50                  55                  60

Gly Ser Leu Asp Leu His Gly Ile Ser Lys Gln Met His Pro Pro Asn
65                  70                  75                  80

Ser Gly Asn Gln Gly Phe Asn Gln Pro Gln Ile Pro Gly Asn Phe Thr
                85                  90                  95

Ile Pro Met Asp Arg Val Thr Glu Pro Asp Asn Ile Ser Asp Gly Val
            100                 105                 110

Gln Leu Gly Gln His Gly Lys Ile Ala His His His His His His Arg
        115                 120                 125

His His Ser Lys Asn His Gly Ser Asp Glu Glu His Asp Met Asn
130                 135                 140

Glu Asp Ala Ala Asp Gly Lys Asp Lys Lys Gly Ser Pro Trp His Arg
145                 150                 155                 160

Met Lys Trp Thr Asp Ser Met Val Lys Leu Leu Ile Thr Ala Val Ser
                165                 170                 175

Tyr Thr Gly Glu Asp Pro Gly Ala Asp Leu Gly Gly Gly Arg Arg Asn
            180                 185                 190

Tyr Ser Met Met Gln Lys Lys Gly Lys Trp Lys Ala Ile Ser Lys Val
        195                 200                 205

Met Gly Glu Arg Gly Cys His Val Ser Pro Gln Gln Cys Glu Asp Lys
210                 215                 220

Phe Asn Asp Leu Asn Lys Arg Tyr Lys Arg Leu Thr Asp Ile Leu Gly
225                 230                 235                 240

Arg Gly Thr Ala Cys Asn Val Val Glu Asn His Ser Leu Leu Asp His
                245                 250                 255

Met Asp Ile Ser Glu Lys Met Lys Glu Asp Ala Arg Lys Ile Leu Asn
            260                 265                 270

Ser Lys His Leu Phe Tyr Glu Glu Met Cys Ser Tyr His Asn Asn Asn
        275                 280                 285

Arg Ile Ser Leu Pro Glu Asp Pro Ala Leu Gln Gln Ser Leu Gln Leu
290                 295                 300

Ala Leu Arg Cys Lys Glu Asp Asn Asp Phe Met Arg His Ala Ser Gly
305                 310                 315                 320

Asp Ala Glu Leu Asp Asp Asp Gln Ser Glu Asp Ser Asp Tyr Glu Glu
                325                 330                 335

Asn Glu Glu Glu His Arg Ala Val Asp Thr Asn Ile Arg Gly Pro Ser
            340                 345                 350

Met His Lys Arg Met Trp His Val Val Asp His Gly Asp Val Gly Phe
        355                 360                 365

Val Thr Ser Cys Ser Asn Asp Gly Ser Gly Arg Ser Asp Pro Tyr Asp
370                 375                 380

```
Val Leu Asp Ile Asn Lys Pro Phe Pro Asp Gly Cys Asp Leu Ala Leu
385                 390                 395                 400

Val Gln Lys Asp Leu Ala Leu Lys Ala Ala Glu Ile Gln Lys His Arg
                405                 410                 415

Leu Gln Ile Glu Thr Lys Ala Val Gln Leu Ala Lys Gln Arg Leu Lys
            420                 425                 430

Trp Glu Met Phe Arg Lys Asn Lys Asp Leu Glu Leu Glu Lys Leu Ala
            435                 440                 445

Leu Glu Asn Glu Gln Met Met Leu Gln Asn Lys Arg Phe Glu Leu Asp
        450                 455                 460

Leu Arg His Lys Glu Leu Glu Leu Glu Ile Lys Ile Lys Gly Asn Ala
465                 470                 475                 480

Asn His Pro

<210> SEQ ID NO 10
<211> LENGTH: 447
<212> TYPE: PRT
<213> ORGANISM: Sorghum bicolor

<400> SEQUENCE: 10

Met Glu Gly Asn Asn Leu Pro Ser Gly Ser Leu Met Gln Gly Ala Ala
1               5                   10                  15

Tyr Gly Asn Leu Asp Leu His His Ser His Met Gln Met Pro Ala
                20                  25                  30

Pro Ser Ser Gly Asn Gln Ala Phe Asn His Ser Gln Met Pro Ala Asn
            35                  40                  45

Phe Pro Ile Cys Leu Asn Gln Val Thr Asp Ser Asp Gln Leu Pro Glu
    50                  55                  60

Phe Gln Phe Gly Glu His Gly Lys Val Ser His His His His
65                  70                  75                  80

His His Gln Gln His Ala Lys Asn Ser Met Ser Asp Asp Glu His
                85                  90                  95

Gly Val His Glu Asp Ala Thr Asp Ser Gln Thr Ser Lys Gly Lys Lys
            100                 105                 110

Gly Ser Ala Trp His Arg Met Lys Trp Thr Asp Ser Met Val Arg Leu
        115                 120                 125

Leu Ile Thr Ala Ala Ser Tyr Ala Gly Glu Asp Pro Gly Ala Asp Leu
    130                 135                 140

Gly Gly Gly Arg Arg Ser Cys Ala Met Met Gln Lys Lys Gly Lys Trp
145                 150                 155                 160

Lys Ala Ile Ser Lys Val Met Gly Glu Arg Gly Cys Leu Val Ser Pro
                165                 170                 175

Gln Gln Cys Glu Asp Lys Phe Asn Asp Leu Asn Lys Arg Tyr Lys Arg
            180                 185                 190

Leu Thr Asp Ile Leu Gly Arg Gly Thr Thr Cys Arg Val Val Ala Asn
        195                 200                 205

Pro Glu Leu Leu Asp Gly Met Thr Asn Leu Ser Asp Lys Met Lys Asp
    210                 215                 220

Asp Ala Arg Lys Ile Leu Ser Ser Lys His Leu Phe Tyr Glu Glu Met
225                 230                 235                 240

Cys Ser Tyr His Asn Asn Asn Arg Phe Ser Leu Pro Glu Asp Pro Ala
                245                 250                 255

Leu Gln Arg Ser Leu Gln Leu Ala Leu Lys Ser Lys Asp Glu His Asp
            260                 265                 270
```

Ala Arg Lys Arg Ala Ser Gly Asp Ala Asp Glu Asp Gln Ser Ala
                275                 280                 285

Asp Thr Asp Tyr Glu Glu Asn Asp Asp Glu His Pro Met Val His
    290                 295                 300

Val Asn Lys Gly Thr Leu Pro Met His Lys Arg Met Arg Tyr Met Ala
305                 310                 315                 320

Ala Asp Met Glu Asp Ala Gly Phe Gly Asn Ser Ser Ser His Asp
                325                 330                 335

Cys Ser Arg Arg Ser Asp Pro His Ser Ile Ala Val Asp Ile Asn Lys
                340                 345                 350

Ala Phe Pro Asp Gly Thr Asn Leu Ala Leu Val Gln Lys Asp Leu Ala
                355                 360                 365

Thr Gln Ser Ala Glu Ile Glu Lys Gln Arg Met Glu Ile Glu Val Glu
    370                 375                 380

Ala Leu Glu Leu Ala Lys Gln Arg Leu Lys Trp Glu Ile Phe Ser Lys
385                 390                 395                 400

Lys Lys Asp Arg Glu Leu Glu Lys Met Arg Leu Glu Asn Glu Gln Met
                405                 410                 415

Lys Met Glu Asn Arg Arg Leu Glu Leu Glu Val Arg Asp Lys Glu Leu
                420                 425                 430

Glu Leu Glu Arg Lys Leu Gln Gly Ser Gly Ser His Ala Met Thr
    435                 440                 445

<210> SEQ ID NO 11
<211> LENGTH: 446
<212> TYPE: PRT
<213> ORGANISM: Setaria italica

<400> SEQUENCE: 11

Met Glu Gly Asn Asn Leu Pro Ser Gly Ser Leu Met Gln Gly Thr Asn
1               5                   10                  15

Tyr Gly Ser Leu Asp Leu His His Asn His Met Gln Met His Ala Pro
                20                  25                  30

Asn Ser Gly Asn Gln Gly Phe Asn His Ser Gln Met Pro Ser Asn Phe
            35                  40                  45

Pro Ile His Leu Asn Gln Val Thr Asp Ser Asp Gln Leu Ser Glu Phe
    50                  55                  60

Gln Phe Gly Glu His Gly Lys Ala Asn His His Gln His His Asn
65              70                  75                  80

Gln Gln His Thr Lys Ile Ser Met Ser Asp Asp Glu Glu His Gly Val
                85                  90                  95

Asn Glu Asp Ala Thr Asp Ser Gln Thr Gly Lys Gly Lys Lys Gly Ser
            100                 105                 110

Ala Trp His Arg Met Lys Trp Thr Asp Ser Met Val Lys Leu Leu Ile
        115                 120                 125

Thr Ala Ala Ser Tyr Thr Gly Glu Asp Pro Gly Ala Asp Ser Gly Gly
    130                 135                 140

Arg Arg Asn Cys Ala Met Met Gln Lys Lys Gly Lys Trp Lys Ala Ile
145                 150                 155                 160

Ser Lys Val Met Gly Gln Arg Gly Cys Leu Val Ser Pro Gln Gln Cys
                165                 170                 175

Glu Asp Lys Phe Asn Asp Leu Asn Lys Arg Tyr Lys Arg Leu Thr Asp
            180                 185                 190

Leu Leu Gly Arg Gly Thr Thr Cys Arg Ile Val Ala Asn Pro Glu Leu

```
              195                 200                 205
Leu Asp Ser Met Ala Asn Leu Ser Asp Lys Thr Lys Asp Asp Ala Arg
210                 215                 220

Lys Ile Leu Ser Ser Lys His Leu Phe Tyr Glu Glu Met Cys Ser Tyr
225                 230                 235                 240

His Asn Asn Asn Arg Phe Ser Leu Pro Glu Asp Pro Ala Leu Gln Arg
                245                 250                 255

Ser Leu Gln Leu Ala Leu Lys Cys Lys Asp Glu His Asp Thr Arg Arg
            260                 265                 270

Arg Ala Ser Gly Asp Ala Asp Glu Asp Asp Gln Ser Ala Asp Thr Asp
        275                 280                 285

Tyr Glu Glu Asn Asp Asp Glu His Pro Val Val His Val Asn Lys
290                 295                 300

Gly Thr Leu Pro Val His Lys Arg Met Arg Tyr Met Ala Asp Gln Glu
305                 310                 315                 320

Asp Val Gly Phe Gly Asn Ser Ser Ser His Asp Cys Ser Arg Arg
                325                 330                 335

Ser Asp Pro Leu Ser Ile Thr Val Asp Ile Asn Lys Val Phe Pro Asp
            340                 345                 350

Gly Thr Asn Leu Ala Leu Val Gln Lys Asp Leu Ala Thr Gln Ser Ala
        355                 360                 365

Glu Ile Glu Lys Gln Arg Met Glu Ile Glu Ala Glu Leu Glu Leu
370                 375                 380

Ala Lys Gln Arg His Lys Trp Glu Arg Phe Ser Lys Lys Asp Arg
385                 390                 395                 400

Glu Leu Glu Lys Met Arg Leu Glu Asn Glu Gln Met Lys Ile Glu Asn
                405                 410                 415

Arg Arg Leu Glu Leu Glu Val Arg His Lys Leu Glu Leu Glu Leu
            420                 425                 430

Arg Leu Lys Gly Asn Arg Ser Gln Ala Trp His Asp Asn Ile
        435                 440                 445

<210> SEQ ID NO 12
<211> LENGTH: 563
<212> TYPE: PRT
<213> ORGANISM: Unknown
<220> FEATURE:
<223> OTHER INFORMATION: SAB18 polypeptide

<400> SEQUENCE: 12

Met Glu Gly Asn Leu Ser Gln Gly Gly Ile Val Gln Gly Gly Gly
1               5                   10                  15

Ser Phe Gly Gly Phe Asp Leu Pro Gly Ser Met Arg Val His Arg Gln
                20                  25                  30

Gly Gln His Pro His Thr Met Asn Gln His Gln Ala His Pro Cys Gln
            35                  40                  45

Gly Pro Ala Val His Ser Ser Ile Asn Glu Gly Phe Pro Leu Thr Met
        50                  55                  60

Gly Thr Leu Lys Asn Cys Asp Gln Thr Met Ser Met Asn Glu Phe Ser
65                  70                  75                  80

Gln Gly Asp Arg Asn Lys His Ser Gly Ser Glu Asp Glu Pro Glu
                85                  90                  95

Glu Gly Gly Asp Gly His His Gln Glu Gly Ser Arg Gly Lys Lys Gly
            100                 105                 110

Ser Pro Trp Gln Arg Val Lys Trp Thr Asp Lys Met Val Arg Leu Leu
```

```
            115                 120                 125
Ile Thr Ala Val Ser Tyr Ile Gly Glu Asp Gly Ser Glu Gly Gly
130                 135                 140

Ser Gly Gly Arg Arg Lys Phe Ala Val Leu Gln Lys Lys Gly Lys Trp
145                 150                 155                 160

Lys Ser Ile Ser Lys Val Met Ala Glu Arg Gly Tyr Arg Val Ser Pro
                165                 170                 175

Gln Gln Cys Glu Asp Lys Phe Asn Asp Leu Asn Lys Arg Tyr Lys Arg
            180                 185                 190

Leu Asn Asp Met Leu Gly Arg Gly Thr Ser Cys Gln Val Val Glu Asn
        195                 200                 205

Pro Ala Leu Leu Asp Val Ile Glu Tyr Leu Asn Glu Lys Glu Lys Asp
210                 215                 220

Asp Val Arg Lys Ile Leu Asn Ser Lys His Leu Phe Tyr Glu Glu Met
225                 230                 235                 240

Cys Ser Tyr His Asn Cys Asn Arg Leu His Leu Pro His Asp Pro Ala
                245                 250                 255

Leu Gln Arg Ser Leu Gln Ile Ala Leu Arg Asn Arg Asp Asp His Asp
            260                 265                 270

Asn Asp Asp Val Arg Arg Ser Tyr His Asp His Asp Glu Asp Asp
        275                 280                 285

His Asp Met Glu Thr Asp Asp His Asp Glu Phe Glu Glu Asn Tyr Ala
290                 295                 300

Ser His Gly Asp Ser Arg Val Ile Phe Gly Gly Leu Gly Gly Thr Pro
305                 310                 315                 320

Lys Arg Leu Arg Gln Gly Gln Gly His Glu Asp Ala Thr Thr Phe Gly
                325                 330                 335

Asn Ser Phe Asn Cys Gln Asp Tyr His Lys Ser Pro Tyr Pro His Gly
            340                 345                 350

Gln Met Val Gln Pro Asp Gly Asn His Ala Leu Pro Glu Asn Met Lys
        355                 360                 365

Ala Ala Trp Leu Gln Lys Gln Trp Ile Glu Ser Arg Ser Val Gln Leu
370                 375                 380

Glu Glu Gln Lys Leu Gln Ile Gln Val Glu Met Met Glu Leu Glu Lys
385                 390                 395                 400

Gln Lys Phe Lys Trp Glu Arg Phe Ser Lys Lys Asp Arg Glu Leu
                405                 410                 415

Glu Lys Phe Lys Leu Glu Asn Asp Arg Met Lys Ile Glu Asn Glu Arg
            420                 425                 430

Ile Ala Leu Glu Leu Lys Arg Lys Glu Ile Gly Gly Thr Ile Tyr Ser
        435                 440                 445

Phe Asp Gly Glu Thr Asp Gly Met Val Val His Asp Thr Ser Ala
450                 455                 460

Ser Ile Gln Gly Leu Gly Gly Pro Met Thr Arg Ala Arg Thr Lys Lys
465                 470                 475                 480

Ala Lys Glu Ala Leu Thr Gln Leu Val Ala Lys Val Leu Glu Ser Lys
                485                 490                 495

Pro Thr Leu Glu Ser Met Glu Asp Lys Met Val Met Cys Ile Lys Pro
            500                 505                 510

Leu Glu Glu Gly Trp Gly Ala Ser Leu Ala Gly Cys Asn Cys Val Ile
        515                 520                 525

Thr Leu Asp Arg Asn Cys Val Glu Val Arg Phe Leu Asp Ala Leu
530                 535                 540
```

```
Leu Leu Pro Tyr Phe Val Val Ser Val Arg Ala Val Val Gln Gln
545                 550                 555                 560

Gly Val Leu
```

<210> SEQ ID NO 13
<211> LENGTH: 420
<212> TYPE: PRT
<213> ORGANISM: Populus trichocarpa

<400> SEQUENCE: 13

```
Met Glu Gly Asn Leu Ser Gln Gly Gly Met Ile Pro Gly Gly Ala Pro
1               5                   10                  15

Phe Gly Gly Leu Asp Leu Gln Gly Ser Met Arg Val His His Gln Ala
                20                  25                  30

Gln His Pro His Thr Met His His Gln His Pro Leu His Arg Gln
            35                  40                  45

Gly Ser Ser Thr Leu Thr Ser Val Glu Glu Gly Phe Pro Leu Thr Met
    50                  55                  60

Gly Phe Met His Asn Ser Asp Gln Asn Ile Ser Met Thr Asp Tyr Asn
65                  70                  75                  80

Lys Gly Asp Arg Gly Lys Asn Ser Val Ser Asp Glu Asp Glu Pro Ser
                85                  90                  95

Tyr Thr Glu Glu Gly Ala Asp Gly His Asn Asp Ala Ile Thr Gly Lys
            100                 105                 110

Lys Gly Thr Pro Trp Gln Arg Val Lys Trp Thr Asp Lys Met Val Arg
        115                 120                 125

Leu Leu Ile Thr Ala Val Ser Tyr Ile Gly Glu Asp Gly Thr Ser Asp
130                 135                 140

Cys Gly Gly Gly Met Arg Arg Lys Phe Thr Val Leu Gln Lys Lys Gly
145                 150                 155                 160

Lys Trp Lys Ser Val Ser Lys Val Met Ala Glu Arg Gly Phe His Val
                165                 170                 175

Ser Pro Gln Gln Cys Glu Asp Lys Phe Asn Asp Leu Asn Lys Arg Tyr
            180                 185                 190

Lys Arg Leu Asn Asp Met Leu Gly Arg Gly Thr Ser Cys Gln Val Val
        195                 200                 205

Glu Asn Pro Ala Leu Leu Asp Val Ile Asp Tyr Leu Thr Glu Lys Glu
210                 215                 220

Lys Asp Asp Val Arg Lys Ile Leu Asn Ser Lys His Leu Phe Tyr Glu
225                 230                 235                 240

Glu Met Cys Ser Tyr His Asn Gly Asn Arg Leu His Leu Pro His Asp
                245                 250                 255

Pro Ala Leu Gln Arg Ser Leu Gln Leu Ala Leu Arg Ser Arg Asp Asp
            260                 265                 270

His Asp Asn Asp Asp Ala Arg Arg His Gln His Asp Asp Leu Asp Glu
        275                 280                 285

Asp Asp Gln Glu Ile Glu Thr Asp Asp His Asp Glu Phe Glu Glu Asn
290                 295                 300

His Ala Ser His Gly Asp Cys Arg Gly Ile His Gly Val Leu Gly Gly
305                 310                 315                 320

Ser Ala Lys Arg Pro Arg Gln Gly Gln Gly His Glu Asp Ala Phe Ser
                325                 330                 335

Pro Glu Ser Ser Lys Ala Val Trp Leu Gln Lys Gln Trp Met Glu Ser
            340                 345                 350
```

```
Arg Thr Leu Gln Leu Glu Glu Arg Lys Leu Gln Ile Gln Gln Glu Met
            355                 360                 365

Leu Glu Leu Glu Lys Gln Arg Phe Lys Trp Gln Arg Phe Ser Lys Lys
370                 375                 380

Arg Asp Arg Glu Leu Glu Lys Leu Arg Met Glu Asn Glu Arg Ile Lys
385                 390                 395                 400

Leu Glu Asn Glu Gln Met Ala Leu Glu Leu Lys Arg Lys Glu Met Gly
                405                 410                 415

Ala Asp Phe Asn
            420

<210> SEQ ID NO 14
<211> LENGTH: 385
<212> TYPE: PRT
<213> ORGANISM: Unknown
<220> FEATURE:
<223> OTHER INFORMATION: Arabidopsis sp.

<400> SEQUENCE: 14

Met Glu Gly Asn Cys Ser Gln Gly Arg Phe Asp Ser Gln Val Ser Ser
1               5                   10                  15

Met Arg Asp Leu Arg Pro Asn Ala Ile Asn Gln Asn Gln Lys Gln His
            20                  25                  30

His Pro Asn Ser Arg Gln Asp Ser Gly Phe Asn Thr Met Asp Thr
        35                  40                  45

Arg His Asn Asn Val Asp Arg Gly Lys Lys Ser Met Ser Glu Asp Asp
    50                  55                  60

Glu Leu Cys Leu Leu Ser Ser Asp Gly Gln Asn Lys Ser Lys Glu Asn
65                  70                  75                  80

Ser Pro Trp Gln Arg Val Lys Trp Met Asp Lys Met Val Lys Leu Met
                85                  90                  95

Ile Thr Ala Leu Ser Tyr Ile Gly Glu Asp Ser Gly Ser Asp Lys Lys
            100                 105                 110

Phe Ala Val Leu Gln Lys Lys Gly Lys Trp Arg Ser Val Ser Lys Val
        115                 120                 125

Met Asp Glu Arg Gly Tyr His Val Ser Pro Gln Gln Cys Glu Asp Lys
    130                 135                 140

Phe Asn Asp Leu Asn Lys Arg Tyr Lys Lys Leu Asn Glu Met Leu Gly
145                 150                 155                 160

Arg Gly Thr Ser Cys Glu Val Val Glu Asn Pro Ser Leu Leu Asp Lys
                165                 170                 175

Ile Asp Tyr Leu Asn Glu Lys Glu Lys Asp Glu Val Arg Arg Ile Met
            180                 185                 190

Ser Ser Lys His Leu Phe Tyr Glu Glu Met Cys Ser Tyr His Asn Gly
        195                 200                 205

Asn Arg Leu His Leu Pro His Asp Pro Ala Val Gln Arg Ser Leu His
    210                 215                 220

Leu Ile Thr Leu Gly Ser Arg Asp Asp His Asp Asn Asp Glu His Gly
225                 230                 235                 240

Lys His Gln Asn Glu Asp Leu Asp Asp Asp Tyr Glu Glu Asp
                245                 250                 255

His Asp Gly Ala Leu Ser Asp Arg Pro Leu Lys Arg Leu Arg Gln Ser
            260                 265                 270

Gln Ser His Glu Asp Val Gly His Pro Asn Lys Gly Tyr Asp Val Pro
        275                 280                 285
```

```
Cys Leu Pro Arg Ser Gln Ala Asp Val Asn Arg Gly Ile Ser Leu Asp
        290                 295                 300

Ser Arg Lys Ala Ala Gly Leu Gln Arg Gln Gln Ile Glu Ser Lys Ser
305                 310                 315                 320

Leu Glu Leu Glu Gly Arg Lys Leu Gln Ile Gln Ala Glu Met Met Glu
                325                 330                 335

Leu Glu Arg Gln Gln Phe Lys Trp Glu Val Phe Ser Lys Arg Arg Glu
            340                 345                 350

Gln Lys Leu Ala Lys Met Arg Met Glu Asn Glu Arg Met Lys Leu Glu
        355                 360                 365

Asn Glu Arg Met Ser Leu Glu Leu Lys Arg Ile Glu Leu Gly Ala Lys
    370                 375                 380

Leu
385

<210> SEQ ID NO 15
<211> LENGTH: 509
<212> TYPE: PRT
<213> ORGANISM: Brachypodium distachyon

<400> SEQUENCE: 15

Met Gly Pro Arg Gly Ala Pro Ala Ala Met Leu Gly Met Gly Met Gln
1               5                   10                  15

Gln Phe Val Ser Gln Pro His Ala Ala Pro Val Phe Gln Gln Pro
            20                  25                  30

Glu His Leu His Gly Gly Val Phe Gly Gln His His Gln Pro Val
        35                  40                  45

Pro Ala Pro Ala Arg Gln Gln Pro Ser Tyr Ser Pro Tyr Pro Ala
    50                  55                  60

Val Pro Val Arg Ala Gly Gly His His Glu Glu Ala Met Gly
65                  70                  75                  80

His Gly Ala Gly Asn Asp Gly Val Ala Ala Gln Gln Gln Gln Pro
                85                  90                  95

Gly Gly Leu Trp Ser Arg Met Lys Trp Thr Asp Ala Met Val Arg Leu
            100                 105                 110

Leu Ile Met Val Val Tyr Asn Ala Gly Asp Asp Gly Glu Gly Ala Val
        115                 120                 125

Ala Ala Ala Val Gly Gly Gly Gly Gly Gly Ser Arg Ala Ala
    130                 135                 140

Ala His Gly His Gly His Gly Ser Ala Thr Ala Ala His Ala Gln
145                 150                 155                 160

Gln Lys Lys Gly Lys Trp Lys Ser Val Ser Arg Thr Met Gly Glu His
                165                 170                 175

Gly Phe Thr Val Ser Pro Gln Gln Cys Glu Asp Lys Phe Asn Asp Leu
            180                 185                 190

Asn Lys Arg Tyr Lys Arg Val Val Asp Leu Leu Gly Arg Gly Lys Ala
        195                 200                 205

Cys Ala Val Val Glu Ser Pro Ala Leu Leu Asp Ala Met Asp Glu Leu
    210                 215                 220

Pro Pro Arg Ala Lys Glu Glu Ala Arg Lys Leu Leu Ser Ser Lys His
225                 230                 235                 240

Leu Phe Phe Arg Glu Met Cys Asn Tyr His Asn Ser Pro His Pro His
                245                 250                 255

Ala Ala Ala Ala Val Thr Val Ala Ser His His Gly Ala Ala Val His
```

-continued

```
                260                 265                 270
Asp His Glu Gly Ala Ala Ala Cys Phe His His Pro Gln Pro Val Ala
            275                 280                 285

Cys Ala Ser Ser Ala Ala Ala Leu His Ala Leu Ala Pro Ser Pro Ala
            290                 295                 300

Met Met Asn Ser Ser Thr Arg Thr Glu Gly Asp Glu Glu Asp Asp Asp
305                 310                 315                 320

Ser Glu Asn Ala His Pro Arg Thr Ser Asn Glu Val Glu Glu Met Asp
            325                 330                 335

Glu Glu Asp Val Leu Asp Asp Glu Glu Glu Gln Ala Pro Gly Ile Lys
            340                 345                 350

Ser Lys His Arg Arg Phe His Ser Leu Asn Ser Asn Gly Phe Pro Lys
            355                 360                 365

Arg Arg Arg Gly Glu Ser Ser Thr Met Glu Ala Glu Glu Asp Gly Asn
            370                 375                 380

Asn Asn Asp Asn Thr Gly Ala Gly Glu Gly Glu Ala Pro Ser Ser Ala
385                 390                 395                 400

Gly Val Gln His Leu Gln Ser Glu Leu Ala Ala Ala Gly Gly Gly
            405                 410                 415

Asp Pro Glu Gln Ala Arg Arg Trp Met Arg Arg Arg Ala Leu Ala Val
            420                 425                 430

Glu Glu Gln Leu Leu Ala Cys Asp Tyr Arg Glu Tyr Lys Leu His Arg
            435                 440                 445

Gln Arg Leu Lys Trp Glu Arg Phe Cys Ala Gly Lys Glu Arg Glu Met
            450                 455                 460

Glu Leu Ala Lys Leu Arg Asn Glu Arg Ala Arg Ile Asp Gly Arg Arg
465                 470                 475                 480

Met Leu Leu Met Ile Gln His Lys Glu Ile Asp Leu Ala Gln Gly Leu
            485                 490                 495

Leu Asn Arg Arg Arg Gly Leu Gln Gln Leu Leu Leu Cys
            500                 505
```

DROUGHT AND SUBMERGENCE TOLERANCE IN PLANTS

CROSS-REFERENCE TO RELATED APPLICATIONS

This application claims priority benefit of U.S. Provisional Patent Application No. 62/112,572, filed Feb. 5, 2015; and U.S. Provisional Patent Application No. 62/043,335, filed Aug. 28, 2014, each of which is herein incorporated by reference for all purposes.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy and Grant No. 2010-0195 awarded by the U.S. Department of Agriculture. The government has certain rights in this invention.

REFERENCE TO SUBMISSION OF A SEQUENCE LISTING

This application includes a Sequence Listing as a text file named "077429-0956968_SEQ_ST25" created Nov. 13, 2015 and containing 60,456 bytes. The material contained in this text file is incorporated by reference in its entirety for all purposes.

BACKGROUND OF THE INVENTION

Plant response to changes in environment is complex and interlinked with hormone homeostasis that drive several adaptive responses. Rice varieties that express the SUB1A-1 allele (referred to herein as SUB1A) are tolerant to submergence whereas varieties lacking SUB1A are not. SUB1A exerts is effect by preventing shoot elongation, reducing carbohydrate consumption, preventing chlorophyll breakdown and activating alternative energy pathways. SUB1A has also been reported to promote plants survival during drought stress conditions (Fukao et al., *Plant Cell* 23:412-427, 2011).

SUB1A interacts with various proteins, including SAB18 (Seo et al., *PLoS Genetics* 7:1-12, 2011). SAB18 is a trihelix protein. Sequence analysis indicates the present of a Myb/SANT-like DNA-binding domain, which has been shown to be involved in carbohydrate and nucleotide metabolism. SAB18 has also been postulated as being involved in tolerance to submergence (Seo et al., *PLoS Genetics* 7:1-12, 2011) as a negative regulator. However, the role of SAB18 in conferring tolerance to submergence or drought tolerance has not previously been demonstrated.

BRIEF SUMMARY OF ASPECTS OF THE INVENTION

The invention is based, in part on the discovery that SAB18 is a positive regulator of drought and submergence tolerance. In some aspects, the invention thus provides plants engineered to overexpress SAB18 that have increased tolerance to drought, or submergence, and methods for engineering such plants.

Thus, in one aspect, the invention provides a plant comprising a recombinant nucleic acid comprising a promoter operatively linked to a polynucleotide encoding a SAB18 polypeptide comprising an amino acid sequence at least 70%, 80%, 90%, or 95% identical to the length of the region of SEQ ID NO:2 from position 159 to 231 or to the length of the region of SEQ ID NO:6 from position 159 to 231. In some embodiments, the promoter is heterologous to the polynucleotide. In some embodiments, the SAB18 polypeptide has at least 60%, 70%, 75%, 80%, 85%, 90%, or 95%, or greater, identity to a 400 amino acid region of SEQ ID NO:2 or SEQ ID NO:6 that comprises the SANT domain. In some embodiments, the polypeptide comprises a SANT domain having the sequence of the SANT domain of SEQ ID NO:2 or SEQ ID NO:6. In some embodiments, the SAB18 polypeptide has at least 60%, 70%, 75%, 80%, 85%, 90%, or 95%, or greater, identity to amino acids 1-439 of SEQ ID NO:2 or has at least 60%, 70%, 75%, 80%, 85%, 90%, or 95%, or greater, identity to SEQ ID NO:6. In some embodiments, the SAB18 polypeptide has at least 60%, 70%, 75%, 80%, 85%, 90%, or 95%, or greater, identity to SEQ ID NO:2. In some embodiments, the SAB18 polypeptide has at least 60%, 70%, 75%, 80%, 85%, 90%, or 95%, or greater, identity to amino acids 1-439 of SEQ ID NO:2, with the proviso that the SAB18 polypeptide is not SEQ ID NO:2. In some embodiments, the polypeptide comprises SEQ ID NO:6 or comprises amino acids 1-439 of SEQ ID NO:2. In some embodiments, the polypeptide comprises amino acids 1-439 of SEQ ID NO:2, with the proviso that the polypeptide is not the SATB polypeptide of SEQ ID NO:2. In some embodiments, the SAB18 polypeptide comprises at least 70 contiguous amino acids of SEQ ID NO:2, but less than 100, less than 200, less than 300, or less than 400 contiguous amino acids of SED ID NO:2. In some embodiments, the SAB18 polypeptide comprisescomprises no more that 439 contiguous amino acids of SEQ ID NO:2. In some embodiments, the polypeptide comprises SEQ ID NO:2. In some embodiments, the plant is a monocot. In some embodiments, the plant is a grass, such as rice. In some embodiments, the plant, e.g., a rice plant, expresses Sub1A. In some aspects, the invention provides a plant cell from the plant.

In a further aspect, the invention provides a plant comprising a recombinant nucleic acid comprising a promoter operatively linked to a polynucleotide encoding a polypeptide that comprises a region that has at least 60%, 70%, 75%, 80%, 85%, 90%, or 95% identity, or greater, to the SANT domain of SEQ ID NO:4. In some embodiments, the polypeptide comprises a region that has at least 60%, 70%, 75%, 80%, 85%, 90%, or 95% identity, or greater, to SEQ ID NO:4. In some embodiments, the polypeptide comprises the SANT domain of SEQ ID NO:4. In some embodiments, the polypeptide comprises SEQ ID NO:4. In some embodiments, the plant is a monocot. In some embodiments, the plant is a grass, such as rice. In some embodiments, the plant, e.g., a rice plant, expresses Sub1A. In some aspects, the invention provides a plant cell from the plant.

The invention also provides a method for increasing tolerance of a plant to drought or submergence, the method comprising introducing into plants a nucleic acid comprising a promoter operatively linked to a polynucleotide encoding a SAB18 polypeptide comprising an amino acid sequence at least 70%, 80%, 90%, or 95% identical to the length of the region of SEQ ID NO:2 or SEQ ID NO:6 from position 159 to 231; and selecting a plant with increased drought tolerance or submergence tolerance compared to a plant lacking the nucleic acid. In some embodiments, the promoter is heterologous to the polynucleotide. In some embodiments, the SAB18 polypeptide has at least 60%, 70%, 75%, 80%, 85%, 90%, or 95%, or greater, identity to a 400 amino acid region of SEQ ID NO:2 or SEQ ID NO:6 that comprises the SANT domain. In some embodiments, the SAB18 polypeptide has at least 60%, 70%, 75%, 80%, 85%, 90%, or 95%, or greater, identity to SEQ ID NO:6. In some embodiments, the SAB18 polypeptide has at least 60%, 70%, 75%, 80%, 85%, 90%, or 95%, or greater, identity to amino acids 1-439 of SEQ ID NO:2. In some embodiments, the SAB18 polypeptide has at least 60%, 70%, 75%, 80%, 85%, 90%, or 95%, or greater, identity to SEQ ID NO:2. In some embodiments, the polypeptide comprises the SANT domain of SEQ ID NO:2 or SEQ ID NO:6. In some embodiments, the polypeptide comprises amino acids 1-439 of SEQ ID NO:2 or comprises SEQ ID NO:6. In some embodiments, the polypeptide comprises SEQ ID NO:2. In some embodiments, the plant is a monocot, e.g., a grass plant such as a rice plant. In some embodiments, e.g., when the plant is a rice plant, the plant expresses Sub1A.

The invention further provides a method for increasing tolerance of a plant to drought or submergence, the method comprising introducing into plants a nucleic acid comprising a promoter operatively linked to a polynucleotide encoding a polypeptide comprising a region that has at least 60%, 70%, 75%, 80%, 85%, 90%, or 95% identity, or greater, to the SANT domain of SEQ ID NO:4. In some embodiments, the polypeptide comprises the SANT domain of SEQ ID NO:4. In some embodiments, the polypeptide comprises a region that has at least 60%, 70%, 75%, 80%, 85%, 90%, or 95% identity, or greater, to SEQ ID NO:4. In some embodiments, the polypeptide comprises SEQ ID NO:4. In some embodiments, the plant is a monocot, e.g., a grass plant such as a rice plant. In some embodiments, e.g., when the plant is a rice plant, the plant expresses Sub1A.

BRIEF DESCRIPTION OF THE DRAWINGS

FIG. 1 shows an alignment of illustrative SAB18 polypeptide sequences. (SEQ ID NOS:8-15; SEQ ID NO:6)

FIG. 2 shows an alignment of SEQ ID NO:6 to SEQ ID NO:4.

FIG. 3 shows plant height following submergence of M202(SUB1A) plants in which SAB18 is overexpressed or inhibited compared to control M202(SUB1A) plants and M202 plants. Fourteen-day-old M202, M202 (SUB1), SAB18ox (overexpression) and SAB18 RNAi (inhibited) plants were subjected to submergence. On the left are representative plants following 16 days submergence. On the right are height measurements of these plants. The data represent the mean±SE from 3 independent biological replicates.

DETAILED DESCRIPTION OF THE INVENTION

Definitions

Figure 4:
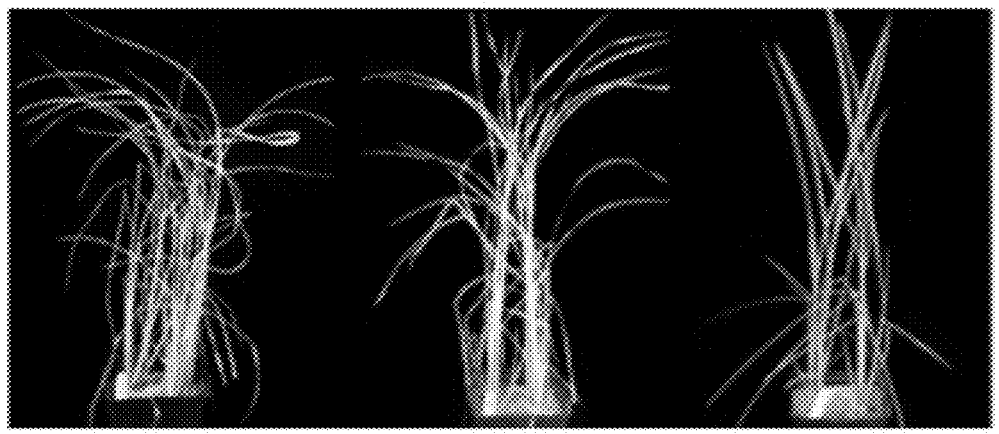
FIG. 4 provides illustrative data showing that M202 (SUB1A) plants that overexpress SAB18 have a drought-tolerant phenotype. Five-week-old M202 (Sub1A) plants and M202(Sub1A plants in which SAB 18 was overexpressed or inhibited (SAB18ox and SAB RNAi, respectively), were subjected to 6 days drought treatment. SAB18ox plants showed a drought tolerant phenotype.

As used herein, the term "SAB18" refers to a trihelix polypeptide that contains a Myb/SANT-like DNA binding domain and is involved in conferring increased abiotic stress tolerance, e.g., drought tolerance and submergence tolerance, in plants when overexpressed. An illustrative SAB18 gene in rice is the locus LOC_Os11g06410. The term "SAB18" encompasses variants and interspecies homologs to the specific polypeptides described herein. A nucleic acid that encodes SAB18 refers to a gene, pre-mRNA, mRNA, and the like, including nucleic acids encoding polymorphic variants, alleles, mutants, and interspecies homologs of the particular amino acid sequences described herein. A SAB18 "gene", as used herein, refers to a SAB18 nucleic acid that encodes a SAB18 protein. Such a gene may be a cDNA. Thus, in some embodiments, a SAB18 nucleic acid encodes a polypeptide having an amino acid sequence that has at least 40% identity, typically at least 45%, 50%, 55% identity, often at least 60%, 65%, 70%, 75%, 80%, 85%, 90%, 91%, 92%, 93%, 94%, 95%, 96%, 97%, 98% or 99% or greater, amino acid sequence identity, preferably over a region of at least about 50 or 100 or 200 or more amino acids amino acids in length, or over the length of the entire polypeptide, to the amino acid sequence of SEQ ID NO:2 or to the amino acid sequence of SEQ ID NO:6. Examples of SAB18 polypeptides encoded by SAB18 nucleic acids are shown in FIG. 1.

The terms "increased level of SAB18 activity" or "increased activity" refer interchangeably to an increase in the amount of activity of a SAB18 protein in a plant, e.g., a grass plant, engineered to increase expression of the SAB18 polypeptide compared to the amount of activity in a wild-type (i.e., naturally occurring) plant. In some embodiments, "increased activity" results from increases in the level of protein in the plant compared to a corresponding wild-type plant. An increased level of activity or increased level of expression can be an increase in the amount of activity or expression of at least 10%, 20%, 30%, 40%, 50%, 60%, 70%, 80%, or 90% or greater, compared to a wildtype plant. Increased expression or activity of SAB18 can be assessed by any number of assays, including, but not limited to, measuring the level of SAB18 RNA transcripts, the level of SAB18 protein, or by measuring the activity, e.g., binding to SUB1A or the ability to confer drought tolerance to a plant compared to a native plant that has not been engineered to overexpress SAB18.

The term "overexpression" in the context of SAB18 expression refers to expressing SAB18 in a plant at a level that is greater than in a corresponding native plant that has not been engineered to overexpress SAB18. "Overexpression" can refer to an increased amount of SAB18 compared to a native plant or to expression at any level in a plant where the corresponding native plant does not express SAB18. Overexpression can occur when, for example, a constitutive promoter directs expression of a nucleic acid encoding SAB18 or overexpression can be induced when an appropriate environmental signal is present, such as drought. Overexpression may occur throughout a plant or in specific tissues of the plant.

The terms "increased tolerance to drought" in the context of this invention refers to an ability of plant to survive low water conditions for a longer period of time, or to recover more quickly, than a control plant. Where a transgenic plant as described herein is tested for tolerance, a control plant can be a corresponding non-transgenic plant from the same plant line.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two polypeptides, refers to a sequence that has at least 40% identity, typically at least 45%, 50%, 55%, or at least 60% sequence identity with a reference sequence. Percent identity can be any integer from 40% to 100%. Some embodiments include at least: 55%, 60%, 65%, 70%, 75%, 80%, 85%, 90%, 91%, 92%, 93%, 94%, 95%, 96%, 97%, 98%, or 99%, compared to a reference sequence, e.g., SEQ ID NO:6, using the programs described herein; preferably BLAST using standard parameters, as described below. For example, a SAB18 polypeptide may have a sequence that is at least 60%, 65%, 70%, 75%, 80%, 85%, 90%, 91%, 92%, 93%, 94%, 95%, 96%, 97%, 98%, or 99% identical to a sequence of SEQ ID NO:6.

The term "substantial identity" in the context of polynucleotide sequences means that a polynucleotide comprises a sequence that has at least 25% sequence identity. Alternatively, percent identity can be any integer from at least 25% to 100% (e.g., at least 25%, 26%, 27%, 28%, ..., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%). More preferred embodiments include at least: 25%, 30%, 35%, 40%, 45%, 50%, 55%, 60%, 65%, 70%, 75%, 80%, 85%, 90%, 95%, or 99% compared to a reference sequence, e.g., SEQ ID NO:1, using the programs described herein; preferably BLAST using standard parameters, as described below. For example, a SAB18 nucleic acid may have a sequence that is at least 40%, 45%, 50%, 55%, 60%, 65%, 70%, 75%, 80%, 85%, 90%, 91%, 92%, 93%, 94%, 95%, 96%, 97%, 98%, or 99% identical to a sequence of SEQ ID NO:1 or SEQ ID NO:7. One of skill will recognize that these values can be appropriately adjusted to determine corresponding identity of proteins encoded by two nucleotide sequences by taking into account codon degeneracy, amino acid similarity, reading frame positioning and the like.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA) or by manual alignment and visual inspection Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1997) *Nucleic Acids Res.* 25: 3389-3402, respectively. Software for performing BLAST analyses is publicly available through the National Center for Biotechnology Information (NCBI) web site. The BLAST algorithm parameters W, T, and X determine the sensitivity and speed of the alignment. Optimal alignment of sequences such as polypeptide sequences for comparison can be conducted using BLASTP set to default parameters.

The BLAST algorithm also performs a statistical analysis of the similarity between two sequences (see, e.g., Karlin &

Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$. Compositional score matrix adjustments for protein database searches are described, e.g., in Altschul et al, *FEBS J.* 272:5101-5109, 2005.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

Polypeptides which are "substantially identical" share sequences as noted above except that residue positions which are not identical may differ by conservative amino acid changes. Conservative amino acid substitutions refer to the interchangeability of residues having similar side chains, e.g., similar charge and/or hydrophobicity. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Examples of conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "promoter," as used herein, refers to a polynucleotide sequence capable of driving transcription in a cell. A "promoter" in the context of the present invention refers to regions or sequence located upstream and/or downstream from the start of transcription and which are involved in recognition and binding of RNA polymerase and other proteins to initiate transcription. A "plant promoter" is a promoter capable of initiating transcription in plant cells.

A "constitutive promoter" in the context of this invention refers to a promoter that is capable of initiating transcription in nearly all cell types, whereas a "cell type-specific promoter" or "tissue-specific promoter" initiates transcription only in one or a few particular cell types or groups of cells forming a tissue. In some embodiments, a promoter is tissue-specific if the transcription levels initiated by the promoter in the tissue are at least 2-fold, 3-fold, 4-fold, 5-fold, 6-fold, 7-fold, 8-fold, 9-fold, 10-fold, 50-fold, 100-fold, 500-fold, 1000-fold higher or more as compared to the transcription levels initiated by the promoter in a different tissue.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., Molecular Cloning—A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system.

Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, RNAi, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a SAB18 polypeptide operably linked to a heterologous promoter. In some embodiments, an expression cassette comprises a polynucleotide sequence encoding a SAB18 polypeptide that is targeted to a position in a plant genome such that expression of the polynucleotide sequence is driven by a promoter, e.g., an endogenous promoter, that is present in the plant. In some embodiments, the SAB18 nucleic acid that is introduced into a plant is heterologous to the plant. In some embodiments, the SAB18 nucleic is endogenous to the plant, but is operably linked to a different promoter.

The term "plant" as used herein can refer to a whole plant or part of a plant, e.g., seeds, and includes plants of a variety of ploidy levels, including aneuploid, polyploid, diploid and haploid. The term "plant part," as used herein, refers to shoot vegetative organs and/or structures (e.g., leaves, stems and tubers), branches, roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, and plant tissue (e.g., vascular tissue, ground tissue, and the like), as well as individual plant cells, groups of plant cells (e.g., cultured plant cells), protoplasts, plant extracts, and seeds. The class of plants that can be used in the methods of the invention is generally as broad as the class of higher and lower plants amenable to transformation techniques, including angiosperms (monocotyledonous and dicotyledonous plants), gymnosperms, ferns, bryophytes, and multicellular algae.

Introduction

The invention is based, in part on the discovery that overexpression of SAB18 increases tolerance of a plant to drought and submergence. Thus, in some aspects, the invention provides methods of genetically engineering plants to overexpress SAB18 and transgenic plants that have been engineered using such methods that have increased tolerance to drought or submergence.

SAB18 Nucleic Acid and Polypeptide Sequences

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009).

SAB18 nucleic acid and polypeptide sequences suitable for use in the invention include SAB18 nucleic acid sequences that encode a polypeptide of SEQ ID NO:6 or SEQ ID NO:2 In some embodiments, nucleic acid and polypeptide sequences suitable for use in the invention include a nucleic acid sequence that encodes a polypeptide of SEQ ID NO:4, or a substantially identical variant. In some embodiments, a nucleic acid that encodes an SAB18 polypeptide of the invention has at least 30% identity, often at least 35%, 40%, 45%, 50%, 55%, or 60% identity; or at least 70%, 75%, 80%, 85%, or 90% identity, to the nucleic acid sequence of SEQ ID NO:1 or to the protein-coding region of SEQ ID NO:7.

SAB18 sequences in the context of this invention are members of the GTγ subfamily of GT transcription factors that contain a trihelix DNA binding domain. Accordingly, in the present invention, a "SAB18" sequence can include GTγ sequences, such as Os02g33770, Os12g06640, Os11g0641, At1g21200, At1g76870, Os01g21590, At3g10040, GmAAK69274, and MtABE80120.

A comparison of SAB 18 illustrative polypeptide sequences is provided in FIG. 1. As shown in FIG. 2, there are highly conserved regions of the polypeptide sequences. These conserved sequences are not strictly conserved 100% across the various plant protein sequences. Thus, for example, one of skill can obtain a variant of a SAB18 polypeptide, e.g., a variant of a SAB18 polypeptide of SEQ ID NO:6, by using the sequence alignments to identify residues within the conserved sequences that would be expected to support SAB18 function as well as residues outside of the conserved regions that would be expected to be tolerant to substitution.

Conserved regions of SAB18 include a SANT domain, which corresponds to positions 159-231 of SEQ ID NO:2 and positions 159-231 of SEQ ID NO:6. In some embodiments, a SAB18 polypeptide overexpressed in accordance with the invention comprises a polypeptide that has at least 60% identity, typically at least 65%, 70%, 75%, 80%, 85%, 90%, 95%, or greater, identity over the length of amino acid sequence 159-231 of SEQ ID NO:2 or the length of amino acid sequence 159-231 of SEQ ID NO:6. In some embodiments, a SAB18 polypeptide overexpressed in accordance with the invention comprises a polypeptide that has at least 80%, 85%, 90%, 95%, or greater, identity over the length of the amino acid sequence 159-231 of SEQ ID NO:2 or the length of amino acid sequence 159-231 of SEQ ID NO:6. In some embodiments, a SAB18 polypeptide overexpressed in accordance with the invention comprises a polypeptide that has at least 70%, 75%, 80%, 85%, 90%, 95%, or greater, identity over the length of any one of the amino acid sequences set forth in FIG. 1.

In some embodiments, a polypeptide overexpressed in accordance with the invention comprises a polypeptide that has at least 60% identity, typically at least 65%, 70%, 75%, 80%, 85%, 90%, 95%, or greater, identity over the length of the SANT domain sequence of SEQ ID NO:4. In some embodiments, a SAB18 polypeptide overexpressed in accordance with the invention comprises a polypeptide that has at least 80%, 85%, 90%, 95%, or greater, identity over the length of the amino acid sequence of SEQ ID NO:4, or over the length of the SANT domain of SEQ ID NO:4.

In some embodiments, a SAB18 polypeptide that is overexpressed in accordance with the invention has at least 65%, 70%, 75%, 80%, 85%, 90%, 95%, or greater, identity to a region of SEQ ID NO:2 or SEQ ID NO:6 of 200, 300, or 400 amino acids in length that comprises the SANT domain. In some embodiments, a SAB18 polypeptide that is overexpressed in accordance with the invention has at least 65%, 70%, 75%, 80%, 85%, 90%, 95%, or greater, identity to SEQ ID NO:6 over its length or over the length of SEQ ID NO:2 from positions 1 to 439. In some embodiments the SAB18 polypeptide encoded by the SAB18 polynucleotide has the amino acid sequence of SEQ ID NO:6 or the amino acid sequence of positions 1 to 439 of SEQ ID NO:2.

In some embodiments, a polypeptide that is overexpressed in accordance with the invention has at least 65%, 70%, 75%, 80%, 85%, 90%, 95%, or greater, identity to a region of SEQ ID NO:4 of 200, 300, or 400 amino acids in length that comprises the SANT domain. In some embodiments, a polypeptide that is overexpressed in accordance with the invention has at least 65%, 70%, 75%, 80%, 85%, 90%, 95%, or greater, identity to SEQ ID NO:4. In some embodiments, the polypeptide has the amino acid sequence of SEQ ID NO:4.

Activity of a variant polypeptide of the invention can be assessed using any number of assays, including assays that evaluate the ability of the variant polypeptide to bind to Sub1A. In some embodiments, activity is measured in rice plants by detecting whether overexpression results in increased drought tolerance. Drought tolerance can be assessed as described below.

Isolation or generation of polynucleotide sequences to be overexpressed can be accomplished by a number of techniques. In some embodiments, oligonucleotide probes based on the sequences disclosed here can be used to identify the desired polynucleotide in a cDNA or genomic DNA library from a desired plant species. Probes may be used to hybridize with genomic DNA or cDNA sequences to isolate homologous genes in the same or different plant species.

Alternatively, the nucleic acids of interest can conveniently be amplified from nucleic acid samples using routine amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying a SAB18 gene in plant can be generated from comparisons of the sequences provided herein. For a general overview of PCR see PCR Protocols: A Guide to Methods and Applications (Innis, M, Gelfand, D., Sninsky, J. and White, T., eds.), Academic Press, San Diego (1990).

SAB18 nucleic acid sequences for use in the invention includes genes and gene products identified and characterized by techniques such as hybridization and/or sequence analysis using exemplary nucleic acid sequences, e.g., SEQ ID NO:1, SEQ ID NO:3, or SEQ ID NO:7.

Preparation of Recombinant Vectors

To use isolated sequences in the above techniques, recombinant DNA vectors suitable for transformation of plant cells, such as rice, or other grass crop plant cells, are prepared. Techniques for transformation are well known and described in the technical and scientific literature. For example, a DNA sequence encoding a polypeptide can be combined with transcriptional and other regulatory sequences which will direct the transcription of the sequence from the gene in the intended cells, e.g., rice, or other grass crop plant cells. In some embodiments, an expression vector that comprises an expression cassette that comprises the SAB18 gene further comprises a promoter operably linked to the SAB18 nucleic acid sequence. In other embodiments, a promoter and/or other regulatory elements that direct transcription of the SAB18 gene are endogenous to the plant and an expression cassette comprising the SAB18 gene is introduced, e.g., by homologous recombination, such that the heterologous SAB18 gene is operably linked to an endogenous promoter and is expression driven by the endogenous promoter.

In some embodiments, the SAB18 gene that is overexpressed in the plant is endogenous to the plant. Alternatively, the SAB18 gene may be from a different plant species.

Regulatory sequences include promoters, which may be either constitutive or inducible, or tissue-specific. In some embodiments, a promoter used to express SAB18 drives expression in one of the following regions of the root: cortex, stele, lateral meristem, zone of elongation, vascular, pre-vascular, or root cap. In some embodiments, the promoter used to express SAB18 expression is a native SAB18 promoter. In some embodiments, the promoter is a Sub1A promoter.

Tissue-Specific Promoters

In some embodiments, a plant promoter to direct expression of a SAB18 gene in a specific tissue is employed (tissue-specific promoters). Tissue-specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, cell walls, including e.g., roots or leaves. A variety of promoters specifically active in vegetative tissues, such as leaves, stems, roots and tubers are known.

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier, *FEBS Lett.* 415:91-95, 1997). A ribulose bisphosphate carboxylase promoters expressed almost exclusively in mesophyll cells in leaf blades and leaf sheaths at high levels (e.g., Matsuoka, *Plant J.* 6:311-319, 1994), can be used. Another leaf-specific promoter is the light harvesting chlorophyll a/b binding protein gene promoter (see, e.g., Shiina, *Plant Physiol.* 115:477-483, 1997; Casal, *Plant Physiol.* 116:1533-1538, 1998). The *Arabidopsis thaliana* myb-related gene promoter (Atmyb5) (Li, et al., *FEBS Lett.* 379:117-121 1996), is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize (e.g., Busk et al., *Plant J.* 11:1285-1295, 1997) can also be used, as well as leaf-specific promoters from other monocots, such as rice.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, (e.g., Di Laurenzio, et al., *Cell* 86:423-433, 1996; and, Long, et al., Nature 379:66-69, 1996); can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto, Plant Cell. 7:517-527, 1995). Also useful are kn1-related genes from maize and other species which show meristem-specific expression, (see, e.g., Granger, *Plant Mol. Biol.* 31:373-378, 1996; Kerstetter, *Plant Cell* 6:1877-1887, 1994; Hake, Philos. Trans. R. Soc. Lond. B. Biol. Sci. 350:45-51, 1995). For example, the *Arabidopsis thaliana* KNAT1 promoter (see, e.g., Lincoln, *Plant Cell* 6:1859-1876, 1994), or orthologous monocot promoters, e.g, from maize or rice, can be used.

A stomata-specific promoter, e.g., the promoter of a modified potato KST1 (Plesch et al., *Plant J.* 28(4):455-64 (2001)), may also be employed.

In some embodiments, the promoter is substantially identical to the native promoter of a promoter that drives expression of a gene involved in secondary wall deposition. Examples of such promoters are promoters from IRX1, IRX3, IRX5, IRX8, IRX9, IRX14, IRX7, IRX10, GAUT13, or GAUT14 genes. Specific expression in fiber cells can be accomplished by using a promoter such as the NST1 promoter and specific expression in vessels can be accomplished by using a promoter such as VND6 or VND7. (See, e.g., PCT/US2012/023182 for illustrative promoter sequences.)

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Constitutive Promoters

A promoter, or an active fragment thereof, can be employed which will direct expression of a nucleic acid encoding a fusion protein of the invention, in all or most transformed cells or tissues, e.g. as those of a regenerated plant. Such promoters are referred to herein as "constitutive" promoters and are active under most environmental conditions and states of development or cell differentiation. Examples of constitutive promoters include those from viruses which infect plants, such as the ubiquitin promoter, cauliflower mosaic virus (CaMV) 35S transcription initiation region (see, e.g., Dagless, *Arch. Virol.* 142:183-191, 1997); the 1'- or 2'-promoter derived from T-DNA of *Agrobacterium tumefaciens* (see, e.g., Mengiste supra (1997); O'Grady, Plant Mol. Biol. 29:99-108, 1995); the promoter of the tobacco mosaic virus; the promoter of Figwort mosaic virus (see, e.g., Maiti, *Transgenic Res.* 6:143-156, 1997); actin promoters, such as the *Arabidopsis* actin gene promoter (see, e.g., Huang, *Plant Mol. Biol.* 33:125-139, 1997); alcohol dehydrogenase (Adh) gene promoters (see, e.g., Millar, *Plant Mol. Biol.* 31:897-904, 1996); ACT11 from *Arabidopsis* (Huang et al., *Plant Mol. Biol.* 33:125-139, 1996), Cat3 from *Arabidopsis* (GenBank No. U43147, Zhong et al., *Mol. Gen. Genet.* 251:196-203, 1996), the gene encoding stearoyl-acyl carrier protein desaturase from *Brassica napus* (Genbank No. X74782, Solocombe et al., *Plant Physiol.* 104:1167-1176, 1994), GPc1 from maize (GenBank No. X15596, Martinez et al., *J. Mol. Biol.* 208:551-565, 1989), Gpc2 from maize (GenBank No. U45855, Manjunath et al., *Plant Mol. Biol.* 33:97-112, 1997), other transcription initiation regions from various plant genes known to those of skill. See also Holtorf, "Comparison of different constitutive and inducible promoters for the overexpression of transgenes in *Arabidopsis thaliana,*" Plant Mol. Biol. 29:637-646, 1995).

Inducible Promoters

In some embodiments, a plant promoter may direct expression of the nucleic acids under the influence of changing environmental conditions or developmental conditions. Examples of environmental conditions that may affect transcription by inducible promoters include anaerobic conditions, elevated temperature, drought or other environmental stress, or the presence of light. Examples of developmental conditions that may affect transcription by inducible promoters include senescence and embryogenesis. Such promoters are referred to herein as "inducible" promoters. For example, the invention can incorporate drought-specific promoter such as the drought-inducible promoter of maize (Busk et al., *Plant J,* 11: 1285-95, 1997); or alternatively the cold, drought, and high salt inducible promoter from potato (Kirch *Plant Mol. Biol.* 33:897-909, 1997).

Alternatively, plant promoters which are inducible upon exposure to plant hormones, such as auxins, may be used to express a SAB18 gene. For example, the invention can use the auxin-response elements E1 promoter fragment (AuxREs) in the soybean (*Glycine max* L.) (Liu, *Plant Physiol.* 115:397-407, 1997); the auxin-responsive *Arabidopsis* GST6 promoter (also responsive to salicylic acid and hydrogen peroxide) (Chen, Plant J. 10: 955-966, 1996); the auxin-inducible parC promoter from tobacco (Sakai, 37:906-913, 1996); a plant biotin response element (Streit, *Mol. Plant Microbe Interact.* 10:933-937, 1997); and, the promoter responsive to the stress hormone abscisic acid (Sheen, *Science* 274:1900-1902, 1996).

Plant promoters inducible upon exposure to chemicals reagents that may be applied to the plant, such as herbicides or antibiotics, are also useful for expressing a SAB18 gene in accordance with the invention. For example, the maize In2-2 promoter, activated by benzenesulfonamide herbicide safeners, can be used (De Veylder, *Plant Cell Physiol.* 38:568-577, 19997); application of different herbicide safeners induces distinct gene expression patterns, including expression in the root, hydathodes, and the shoot apical meristem. A SAB18 coding sequence can also be under the control of, e.g., a tetracycline-inducible promoter, such as described with transgenic tobacco plants containing the *Avena sativa* L. (oat) arginine decarboxylase gene (Masgrau, *Plant J.* 11:465-473, 1997); or, a salicylic acid-responsive element (Stange, *Plant J.* 11:1315-1324, 1997; Uknes et al., *Plant Cell* 5:159-169, 1993); Bi et al., *Plant J.* 8:235-245, 1995).

Examples of useful inducible regulatory elements include copper-inducible regulatory elements (Mett et al., *Proc. Natl. Acad. Sci. USA* 90:4567-4571, 1993); Furst et al., *Cell* 55:705-717, 1988); tetracycline and chlor-tetracycline-inducible regulatory elements (Gatz et al., *Plant J.* 2:397-404, 1992); Röder et al., *Mol. Gen. Genet.* 243:32-38, 1994; Gatz, *Meth. Cell Biol.* 50:411-424, 1995); ecdysone inducible regulatory elements (Christopherson et al., *Proc. Natl. Acad. Sci. USA* 89:6314-6318, 1992; Kreutzweiser et al., *Ecotoxicol. Environ. Safety* 28:14-24, 1994; and heat shock-inducible regulatory elements (Takahashi et al., *Plant Physiol.* 99:383-390, 1992; Yabe et al., *Plant Cell Physiol.* 35:1207-1219, 1994; Ueda et al., *Mol. Gen. Genet.* 250:533-539, 1996).

An inducible regulatory element useful in the transgenic plants of the invention also can be, for example, a nitrate-inducible promoter derived from the spinach nitrite reductase gene (Back et al., Plant Mol. Biol. 17:9 (1991)) or a light-inducible promoter, such as that associated with the small subunit of RuBP carboxylase or the LHCP gene families (Feinbaum et al., Mol. Gen. Genet. 226:449 (1991); Lam and Chua, Science 248:471 (1990)).

Examples of additional promoters include flood-specific promoters, such as LE-ACS7, described in, e.g., Shiu et al., Proc Natl Acad Sci USA. 95(17):10334-9 (1998) and ADH promoters from diverse species, described in, e.g., Hoeren et al., Genetics, 149:479-490 (1998), Olive et al., Plant Mol Biol 2:673-684 (1990), Walker et al., Proc. Natl. Acad. Sci. USA, 84:6624-6629 (1987), and Dolferus et al., Plant Physiol 105:1075-1078 (1994); ROS-inducible promoters, such as a GST6 promoter, described in, e.g., Chen et al., Plant J. 10(6):955-66 (1996), an *Arabidopsis* GST1 promoter, described in, e.g., Levine et al., Cell 79:583-589 (1994), a maize Cat1 promoter, described in Guan et al., Plant J., 22(2):87-95 (2000), and *Arabidopsis* PEX1 promoter, described in, e.g., Lopez-Huertas et al., Embo J, 19(24):6770-6777 (2000; and defense-specific promoters include, e.g., the PR-1 promoters from *Arabidopsis* (see, e.g., Lebel, et al. Plant J. 16(2):223-33 (1998)) and tobacco (Eyal, et al., Plant J. 4(2):225-34 (1993)).

Suitable drought-inducible promoters include a maize rab17 gene promoter (Pla et. al., *Plant Mol. Biol.* 21:259-266, 1993), a maize rab28 gene promoter (Busk et. al., *Plant J.* 11:1285-1295, 1997) and maize Ivr2 gene promoter (Pelleschi et. al., *Plant Mol. Biol.* 39:373-380, 1999). A heat-inducible promoter such as a heat tomato hsp80 promoter from tomato (U.S. Pat. No. 5,187,267) may also be employed.

Additional Embodiments for Expressing SAB18

A further method to increase expression of a SAB18 gene is "activation mutagenesis" (see, e.g. Hiyashi et al. *Science* 258:1350-1353 (1992)). In this method, an endogenous SAB18 gene can be modified to be expressed constitutively, ectopically, or excessively by insertion of T-DNA sequences that contain strong/constitutive promoters upstream of the endogenous gene. As explained below, preparation of transgenic plants overexpressing a gene of the invention can also be used to increase expression of that gene. Activation mutagenesis of the endogenous gene of the invention will give the same effect as overexpression of a transgenic nucleic acid of the invention in transgenic plants. Alternatively, an endogenous gene encoding an enhancer of activity or expression of an endogenous gene of the invention can be modified to be expressed by insertion of T-DNA sequences in a similar manner and activity of genes or polypeptides of the invention can be increased.

Another strategy to increase gene expression can be the use of dominant hyperactive mutants of a gene of the invention by expressing modified transgenes. Use of dominant mutants to hyperactivate target genes is described in Mizukami et al., *Plant Cell* 8:831-845 (1996).

SAB18 nucleic acid sequences of the invention are expressed recombinantly in plant cells as described. As appreciated by one of skill in the art, expression constructs can be designed taking into account such properties as codon usage frequencies of the plant in which the SAB18 nucleic acid is to be expressed. Codon usage frequencies can be tabulated using known methods (see, e.g., Nakamura et al. *Nucl. Acids Res.* 28:292, 2000). Codon usage frequency tables are available in the art (e.g., from the Codon Usage Database at the internet site www.kazusa.or.jp/codon/.)

Additional sequence modifications may be made that are also known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence may also be modified to avoid predicted hairpin secondary mRNA structures.

A vector for overexpressing a SAB18 nucleic also comprises sequences in addition to the SAB18 and promoter sequences. Such sequences include a polyadenylation sequence at the 3'-end of the coding region, which may be from the natural gene, from other plant or from T-DNA; a marker gene that convers a selectable phenotype on plant cells, e.g, a marker gene that encodes biocide resistance, antibiotic resistance, e.g., resistance to kanamycin, G418, bleomycin, or hygromycin, or herbicide resistance, such as resistance to chlorosulfuron or Basta. Other vector sequences are well known in the art.

Production of Transgenic Plants

As detailed herein, the present invention provides for transgenic plants comprising recombinant expression cassettes for overexpressing SAB18 using recombinant technology. It should be recognized that the term "transgenic plants" as used here encompasses the plant or plant cell in which the expression cassette is introduced as well as progeny of such plants or plant cells that contain the expression cassette, including the progeny that have the SAB18 cassette stably integrated in a chromosome.

Once an expression cassette comprising a polynucleotide encoding a SAB18 has been constructed, standard techniques may be used to introduce the polynucleotide into a plant in order to modify gene expression. See, e.g., protocols described in Ammirato et al. (1984) Handbook of Plant Cell Culture—Crop Species. Macmillan Publ. Co. Shimamoto et al. (1989) Nature 338:274-276; Fromm et al. (1990) Bio/Technology 8:833-839; and Vasil et al. (1990) Bio/Technology 8:429-434.

Transformation and regeneration of plants is known in the art, and the selection of the most appropriate transformation technique will be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* mediated transformation. Transformation means introducing a nucleotide sequence in a plant in a manner to cause stable or transient expression of the sequence. Examples of these methods in various plants include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Transformed plant cells derived by any of the above transformation techniques can be cultured to regenerate a whole plant that possesses the transformed genotype and thus the desired phenotype such as enhanced drought-resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally, e.g., in Klee et al. *Ann. Rev. of Plant Phys.* 38:467-486, 1987.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In some embodiments, the plant into which the expression construct comprising a nucleic acid sequence that encodes SAB18 is introduced is the same species of plant from which the SAB18 sequence is obtained, and/or the promoter driving expression of the SAB18 sequence, is obtained. In some embodiments, the plant into which the expression construct is introduced is a different species of plant compared to the species from which the SAB18 and/or promoter sequence is obtained.

Plants into which SAB18 can be assessed for overexpress of SAB18 using any known assay, including analysis of RNA, protein, drought tolerance, or submergence tolerance.

Drought tolerance or submergence tolerance can be assayed according to any of a number of well-known techniques. For drought tolerance, drought stress can be induced by the deprivation of water or educed supply of water to a cell, tissue, organ or organism. For example, drought stress can be simulated by giving plants 80% or 90%, or 95% or less water than a control plant and evaluating the plants by any of a number of standard measures including turgor pressure, growth, yield, leaf or shoot elongation, size, and the like, to determine if the plants are more tolerant to drought stress compared to controls. Other parameters that can be assessed to evaluate tolerance include expression of drought-related genes, relative water content, viability, and lipid peroxidation levels. Similarly, submergence tolerance can be evaluated using well known assays, such as those described in the examples sections and the references cited therein.

Additional Genetic Modifications to a Plant

In some embodiments, a plant that is genetically modified to overexpress SAB18 may also be modified for the expression of other genes. For example in some embodiments, a plant may be additionally modified to overexpress SUB1A. SUB1A is an Ethylene Responsive Factor (ERF) transcriptional regulator (Jung et al., *Plant Physiol.* 152:1674-1692, 2010). Sub1A sequences are known (e.g., Xu et al, *Nature* 442:705-708, 2006). Illustrative Sub1A nucleic acid and polypeptide sequences are provided under gene accession DQ011598 and protein accession AAZ06209.1. In some embodiments, a plant is genetically modified to express Sub1A by introducing a nucleic acid encoding a Sub1A polypeptide having at least 60%, 65%, 70%, 75%, 80%, 85%, 90%, 91%, 92%, 93%, 94%, 95%, 96%, 97%, 98% or 99% to SEQ ID NO:5. In some embodiments, the Sub1A polypeptide has at least 60%, 65%, 70%, 75%, 80%, 85%, 90%, 91%, 92%, 93%, 94%, 95%, 96%, 97%, 98% or 99% to a 400 amino acid region of SEQ ID NO:5, or to a 500 amino acid region of SEQ ID NO:5, or to a 600 amino acid region of SEQ ID NO:5.

SUB1A expression constructs can be generated and introduced into plants as described for SAB18. In some embodiments, a SUB1A polynucleotide may be contained within the same expression vector as SAB18. Alternatively, the SUB1A polynucleotide may be introduced into a plant independently. In other embodiments, a plant that overexpresses SUB1A need not be generated using recombination technology, but can be obtained using hybridization and/or mutagenesis and selection.

Methods of Using Plants Having Modified SAB18 Expression

The nucleic acid constructs of the invention can be used to enhance drought tolerance in any plant, but in particular rice or other grass plants. The plant may be a monocotyledonous plant or a dicotyledonous plant. In some embodiments of the invention, the plant is a monocot, e.g., sugarcane, miscanthus, switch grass, oats, wheat, barley, maize, rice, banana, yucca, onion, asparagus, sorghum and hybrids thereof. In some embodiments, the plant is a cereal plant, such as a rice, maize, wheat, barley, millet, rye, triticale, sorghum, or oat plant. In some embodiments, the plant is a green field plant. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*. In some embodiments, the plant is a crop plant, such as a rice, maize, millet, wheat, sorghum, or barley plant. In some embodiments, the plant is an ornamental plant. In some embodiment, the plant is a vegetable- or fruit-producing plant.

EXAMPLES

The following examples are provided to illustrate, but not limit the claimed invention.

Example 1. SAB18 Overexpression Enhances Submergence Tolerance

To assess SAB18 function in drought tolerance, we overexpressed and silenced SAB18 in the rice strain M202 (SUB1), which expresses SUB1A, using *Agrobacterium*-mediated transformation. Plants were evaluated for increased tolerance to submergence stress and drought stress.

Two independently transformed M202 (SUB1) lines overexpressing SAB18 display a rolled leaf phenotype. Submergence stress assays revealed that these lines also displayed enhanced tolerance to submergence. After 16 days of submergence treatment in which the plants are completely submerged in water, the lengths of leaves in SAB18ox lines (which overexpress SAB18) were significantly shorter than the lengths of the leaves of M202 and M202 (SUB1) lines (FIG. 3).

Example 2. SAB18 Overexpression Enhances Drought Tolerance

It has recently been demonstrated that the SUB1A genotypes display enhanced tolerance to drought (Fukao et al. 2011). To determine whether SAB18 overexpression plays a role in drought tolerance, we subjected two SAB18 M202 (SUB1) overexpression genotypes to 6 days of drought stress. The results showed that the SAB18 over-expressing strain (SAB18ox in the Sub1A background) had leaves that remained remarkably erect and green (FIG. 4). The leaves are greener and more erect than plants carrying SUB1A. These results indicated that SAB18 serves an important role in Sub1A-mediated response to submergence and drought stress.

It is understood that the examples and embodiments described herein are for illustrative purposes only and that various modifications or changes in light thereof will be suggested to persons skilled in the art and are to be included within the spirit and purview of this application and scope of the appended claims. All publications, patents, accession numbers, and patent applications cited herein are hereby incorporated by reference in their entirety for all purposes.

Illustrative Sequences

```
SEQ ID NO: 1 SAB18 Coding sequence, LOC_Os11g06410.1
ATGTCTATCCTCCTTTGGCTATCCCATGTACTGCTGAAACTTCATTACTTGAGGTTAT

ATTCATGTGCATCCTCGTGCACTCCTGTGTCCATCTTATATGGTACCAACAAGAAGTT

GAAGTGTTTGGGTGATCGCTTTGGGGAAATGGAAGGCAGCAACCCACCTGGTAATA

TGACACAGGGACCTTCCTATGGGAGTTTAGATTTGCATGGTATCTCCAAGCAAATGC

ATCCTCCAAACTCAGGAAATCAGGGCTTCAACCAGCCTCAGATACCAGGGAATTTTA

CCATTCCTATGGATAGGGTTACAGAGCCTGATAACATCTCTGATGGAGTTCAGTTAG

GACAACATGGGAAGATTGCCCATCATCACCATCACCACAGACACCACTCAAAGAAC

CATGGGAGTGAGGAAGAGGAGCACGATATGAATGAGGATGCTGCTGATGGCAAAG

ACAAGAAGGGCTCTCCATGGCATCGGATGAAGTGGACAGATTCAATGGTGAAGCTT

TTGATTACTGCAGTATCCTACACAGGGGAGGATCCTGGAGCTGATTTAGGCGGTGGG

AGGAGGAACTATTCAATGATGCAAAAGAAGGGAAAATGGAAAGCAATATCAAAGG

TCATGGGCGAGAGAGGTTGCCATGTGTCGCCACAGCGGTGTGAGGATAAGTTCAAT

GACCTTAATAAGAGATACAAAAGACTAACAGATATCCTTGGAAGGGGTACTGCTTG

TAATGTTGTGGAGAATCACTCACTTCTTGATCACATGGATATTTCTGAGAAGATGAA

AGAGGATGCAAGGAAGATACTGAACTCCAAACACTTGTTCTATGAAGAGATGTGTT

CCTACCATAATAATAACCGTATAAGTCTGCCTGAAGATCCCGCACTTCAGCAGTCAC

TACAGCTTGCTCTTAGATGTAAAGAGGATAATGATTTCATGAGGCATGCAAGTGGAG

ATGCTGAACTAGATGATGATCAGAGTGAAGATTCAGATTATGAGGAGAATGAGGAA

GAACATCGAGCAGTTGATACCAATATAAGGGGCCCCTCAATGCATAAAAGGATGTG

GCATGTTGTAGATCATGGTGATGTAGGTTTTGTCACCTCATGCTCGAATGATGGTAG

TGGGAGGTCTGATCCCTATGACGTGTTGGATATCAACAAACCCTTTCCAGATGGATG

TGATTTGGCTTTGGTGCAAAAAGACTTGGCTCTGAAAGCAGCAGAGATTCAAAAAC

ATCGTTTGCAGATTGAAACCAAGGCTGTGCAACTCGCAAAGCAACGTCTCAAGTGG

GAGATGTTCAGGAAGAACTAGGACTTGGAATTGGAAAAGTTGGCGTTGGAGAATGA

ACAAATGATGCTTCAGAATAAGCGGTTTGAGCTTGACCTAAGACACAAGGAGCTAG

AACTTGAGATTAAGATAAAGGGCAATGCTAATCATCCATGA

SEQ ID NO: 2 SAB18 polypeptide sequence, LOC_Os11g06410.1
The SANT domain is underlined
M S I L L W L S H V L L K L H Y L R L Y S C A S S C T P V S I L Y G T N K K L K C L G D R F G E M E G S N P P G N M T Q G P S Y G S L D L H G I S K Q M H P P N S G N Q G F N Q P Q I P G N F T I P M D R V T E P D N I S D G V Q L G Q H G K I A H H H H H R

H H S K N H G S D E E E H D M N E D A A D G K D K K G S P W H R M K W T D S M V

K L L I T A V S Y T G E D P G A D L G G G R R N Y S M M Q K K G K W K A I S K V M

G E R G C H V S P Q Q C E D K F N D L N K R Y K R L T D I L G R G T A C N V V E N H

S L L D H M D I S E K M K E D A R K I L N S K H L F Y E E M C S Y H N N N R I S L P E

D P A L Q Q S L Q L A L R C K E D N D F M R H A S G D A E L D D D Q S E D S D Y E E

N E E E H R A V D T N I R G P S M H K R M W H V V D H G D V G F V T S C S N D G S G
```

-continued

R S D P Y D V L D I N K P F P D G C D L A L V Q K D L A L K A A E I Q K H R L Q I E T
K A V Q L A K Q R L K W E M F R K N K D L E L E K L A L E N E Q M M L Q N K R F E
L D L R H K E L E L E I K I K G N A N H P Stop SEQ ID NO: 3 SAB18 LOC_Os11g06410.1 gene sequence
```
GTTCAGCTTTGGCATTTTCTTCTGAGAAAGAGAAACCTCGTGCTCGGCGAGGCCCAA
TATTTCGGCGGAGGCTGAGGCGGAGGCGGAGGCGGATTGTCTCCTCGCCGGCGTTC
AGTTCAGTCGCCGGATACCGTCGTGAGTCAGCTCTCCTTTTCCCTCCCGATGCATCGC
TTTGTTGGTCGCAGCGGCTTCCGCTGTCATCGCGTGGGGGCGTTAAACCCAATGAGT
TTTTTGTGTGTGCGTGTGTGTGTGTGTGGGGGGGGGGGGTACTCGCCGCTCGGA
TCGCTGGCGACGAGCACTCCGCGTAGGCTCGTCGCGGCCACGTACGCCATCCCGAG
CTCGGGGGCTACCCCGGTCGGAGGCGGAGCGCTTGGGGGCCGGGGTTTAATCGTGC
GGAGGACTCGGTAGGGCTCGCCATACCTCGCGCCGTCCGGCGGCGCAGAGCGCGGC
GTCGCCGCTGGGGAGAAGGACGGACTCAACGAGACGAGCGAGCGACGGCCGACAG
GCGAAGGCGTTCTCGCTTCTTGGCCTCTCGCCGTTGAATTGGAGACCCACATTGGGC
TTGTTTTGTGTGTTACTAGCATCACCAAGAGTTCCCCTACTACTCCCAATTTCAAATT
TTGGGGTTTTTCGAGCAAAAAAAATGGATCCAACAGATATCCAAACCAGCTTCCAA
AAATTTTGAGACCCTAATCCCGTGTTTCCGTTCTCCACCAGTAGAGAATACCTCCCG
CTCCCAATCCACTGCAGCCGGGCAGTTTTCGCGCGCTGCCGAGGTGCTTGGTTCCCC
CATCTCCATTGATTCCCCATCTCGTGCGATTGGCGGAGCTGATGAGTGACGACAGCC
ACGGGCGAGCGGGAGGTGGCACGTCGACAGGCGGCGGAGGGCCGCCAGCGCAGCT
GCGGCAGCCGGCAAGGGCGGCTGGGTGGGCTGCAGGCTGTGGCTGCAGTTGGGCAG
CGCGGCAGTAGCAGGTGGCGGGCCAACAAGTAGCAGGGCAGGCCGGCAGCAGCAG
CAGATCAACAGGATGATTCAATCTTTGCTATTTGCCTTATCCACCTTAAAGATAGCCT
ATTAATCGATCCATCTTTGCTAGGAGTATCTGTTTTGCAGATTATTTATATGTCTATC
CTCCTTTGGCTATCCCATGTACTGCTGAAACTTCATTACTTGAGGTAATTTTTAGTGT
CATGAGGGGTTGTTGTCATGCTTAATATAGACTTGTTAAGATAATATTGTGTGGTAC
AATGTGGTGCAATTTGAGAATTTTTTTCCCATTATTCTTGGGTTGATTCTCATGATAA
TTCATGAGCCACACCTCTTCTTTTTTTAGTCCTCTGCCACTGATCGTGCGTGTGAGAA
TTTGATAGTTTATATTTTGGTGTGGTTCGTGGATTATTATTACACATGGACAGCTAAT
TTGCGCACGACACTTTGTTTTACTATTTTTTCTTGTGAGGTGACAAATTGATTTATTT
TTCCCCATGCATTTTCTTCTCGTTAGTTATGAGTAGCATGGAAAGGTTGCAACATTTT
TTTGTTTTGGCTAGTGGTTGATTGGTTGCCACTTGCCACTGCAATAATGTTTTAAAAT
TGTTCCACTCACATTACCCAGTGGAGTAATATGGTTTGATTTGTCATTTGTGCTGCTG
ATTAATTAGGTTGTTGGTTGATGCAGTTTAGATTCTTCAGAACACTCTGATTTTAGT
GCTCCAATATTATCTTGCTTTGGCAATTATGACAACTATAGGAGGCTGAAATTACCC
TTTATTGTGTAACACTGATTTAAAATCTCTTCAAATTTGTGCATTAGTTATTTCTTATT
AGGTGGCCCTGATTACATATGGACTCTAGTTAAGATATATTGTGTGATTCTGAAGAT
CTTTTTCTTTTAGCAAATTGATTCTGAAGATTGAGATGTATAGAAATGTGCAATATAC
ATGTGTTGGATTTCCAAAAATTCATACCAAACTGCCATTTCAGGTTATATTCATGTGC
ATCCTCGTGCACTCCTGTGTCCATCTTATATGGTACCAACAAGAAGTTGAAGTGTTT
GGGTGATCGCTTTGGGGAAATGGAAGGCAGCAACCCCACCTGGTAATATGACACAGG
```

-continued

```
GACCTTCCTATGGGAGTTTAGATTTGCATGGTATCTCCAAGCAAATGCATCCTCCAA

ACTCAGGAAATCAGGGCTTCAACCAGCCTCAGATACCAGGGAATTTTACCATTCCTA

TGGATAGGGTTACAGAGCCTGATAACATCTCTGATGGAGTTCAGTTAGGACAACATG

GGAAGATTGCCCATCATCACCATCACCACAGACACCACTCAAAGAACCATGGGAGT

GATGAAGAGGAGCACGATATGAATGAGGATGCTGCTGATGGCAAAGACAAGAAGG

GCTCTCCATGGCATCGGATGAAGTGGACAGATTCAATGGTGAAGCTTTTGATTACTG

CAGTATCCTACACAGGGGAGGATCCTGGAGCTGATTTAGGCGGTGGGAGGAGGAAC

TATTCAATGATGCAAAAGAAGGGAAAATGGAAAGCAATATCAAAGGTCATGGGCGA

GAGAGGTTGCCATGTGTCGCCACAGCAGTGTGAGGATAAGTTCAATGACCTTAATA

AGAGATACAAAAGACTAACAGATATCCTTGGAAGGGGTACTGCTTGTAATGTTGTG

GAGAATCACTCACTTCTTGATCACATGGATATTTCTGAGAAGATGAAAGAGGATGCA

AGGAAGATACTGAACTCCAAACACTTGTTCTATGAAGAGATGTGTTCCTACCATAAT

AATAACCGTATAAGTCTGCCTGAAGATCCCGCACTTCAGCAGTCACTACAGCTTGCT

CTTAGATGTAAAGAGGATAATGATTTCATGAGGCATGCAAGTGGAGATGCTGAACT

AGATGATGATCAGAGTGAAGATTCAGATTATGAGGAGAATGAGGAAGAACATCGAG

CAGTTGATACCAATATAAGGGGCCCCTCAATGCATAAAAGGATGTGGCATGTTGTA

GATCATGGTGATGTAGGTTTTGTCACCTCATGCTCGAATGATGGTAGTGGGAGGTCT

GATCCCTATGACGTGTTGGATATCAACAAACCCTTTCCAGATGGATGTGATTTGGCT

TTGGTGCAAAAAGACTTGGCTCTGAAAGCAGCAGAGATTCAAAAACATCGTTTGCA

GATTGAAACCAAGGCTGTGCAACTCGCAAAGCAACGTCTCAAGTGGGAGATGTTCA

GGAAGAACAAGGACTTGGAATTGGAAAAGTTGGCGTTGGAGAATGAACAAATGATG

CTTCAGAATAAGCGGTTTGAGCTTGACCTAAGACACAAGGAGCTAGAACTTGAGAT

TAAGATAAAGGGCAATGCTAATCATCCATGATCTTTGTTCTGTTAGCACTTCATTTCG

CAATATGGTAAGCAAATGGACTAGATTTTCAGTTACTTTTACTAAAAAATGCTCAAT

GTTTATAATTTGGGTAGCTTCTTGTGGGAGTTTTTTCATGACAAGTTTTTAGGTAGTA

CTGTGCTACTAGTGTATATGGAACTATGGAAATCATGCATTGGGGCTGTTTCCTATT

GATAGTGTTTACTTCAGCTTTATAGTCCCAAACCCCTGTAGTACAAAAATTAGTCCC

ATCCATAGATAGAGGCGGCATCAGTTTTTGACGGAGATTTTACTGTTCTACAGCAAA

GAAGGCATCAGTTAGATATGTACTATCAACTGGGAGTTATTTCGTGACTAGTATTAA

GATCAACTGCAATGACTGTGGTTCTATACATGGTGTACTTGGGTGTAAACATAATCA

GCGAATAAAAGATAACAAAAGGGAAGCAACTGCATCACCAAGATACAAATAGTGA

TGCTGCTCGGATTTGGTGATCTTGTGTGCTGTCAGATTGGCACTTCCAAGCTGAGTTT

CAATATCCAATAATCTTCATGATTCAAAGTCAACAATATCCAAATTTTTCTTTTTCCC

CTGATTAAACAGATATTAGTTCTTACTCTTGTATGGATAAGTTGTTAATGGGTAATTG

GTATGGTGTTTGTTATCTTGACAAGAAGTAGCTTATATTTGTTCAATTGCACGAACA

ATGTTTACAGTTTGTCTGTATGTAGAACACTGCTTTTAAATATGATGGTATGCTTTAT

TACAGAGAGTTTACTCTAAAACTCGTAAGTATATAACTGATGAGTCTAGCTTAGCTG

GTTCACCTATGCTTAGCCAACTCCATCGTTTGCTCTTTAGCTTATCAACCACAGCCAA

AATTTGAATTTAAATCTTAAATTTATGGCTAATTTTAGCGAAAATATGTGACTTAAC

TCTGAACGTTTGCCTCTAAAACAGATTACATTGTTATAGTTTTTTCTAAAATGGATTG
```

```
CAGATGGTTATCAGGGTAGCATCCTGTTATTTTCTGCATTGAGTTTTGTTTCTTCCAT

GCTCTTCCAATAATTCCAAGTTCTCTCTAGAACTGAATAATGGTTGTCTGAAACTCA

ATTCGTTCCCCGGATTGTTAATTTCAGGTTGCAGATCAATTCAATTCAGGACCGTGTT

TATGCAAGATGGTAGAGGTGGCAGATTGTTTATGCAAGATGGTAGAGGTGGCAGAT

TATCTGTGACTACTGACAAGTGACAACAATTTCAATGCTTTATAGCTAGCTCAGTGA

TCCTCTCCTCTTGTTGTTTATATATCATTATATCTCCTGATTCTCTCTACTTGTAAAAT

TTCCATGTGATACTGGGCTCCATCTGTATTCTAAAGTTTTCATCATTTTTTTCTATCCA

ACTTTGTTTTACTCAATCAA

SEQ ID NO: 4 Protein sequence for LOC_Os12g06640
The SANT domain is underlined.
MEGNNLPSGSLMRSNSGQMHAPNPGKQGFDHTQMPGNLSMHVNQSTDSDHLSEFQFG

ELGKVDHHHHHHHRQHAKNGMSDDEEHGVNEDATDSQSGKGKKGAAWQRMKWTDS

MVKLLITAVSYTGEDPGADSGAGKRNSAIMQKKGKWKAISKVMGERGCSVSPQQCED

KFNDLNKRYKRLTDILGRGTACKIVENHALLDCMSNLSDKMKDDARKILSSKHLFYEE

MCSYHNNNRVSLPEDPALQRSLQLALRCKDEHDLRRGTSGDADEDDQSVDSDSEEEND

EENYTLQGDKSALPMHKRLRLMTDQEDVGFGNSSSSHGCSRRSDSHGISLDINKAFPDG

TNLALAQKDLATQSADLEEQRLQIEVQAVYLAKQRLKWERFSKNKDRELEQMRLENEK

MRLENKRLELEVRHKELELELKQKGSGNHA

SEQ ID NO: 5 Illustrative SUB1A rice polypeptide sequence
MSNTYTRWIHHGEPLVMVTGNVEHLNEDIGCNVEHLNEDVSCNVEFETNEPPDDPEDD

QMYRMVQDLYPDQNHGPRTKSKFATILEEMKQVLHPGGPYTRFSFVVKLLHIKSFYRIS

NVAFSAFLDLLSSAFPNCSLPASYAEAKTFIRALGLGYESIHVCPNNCVLFRKELAKKDA

CPICGASRWKDADSRRKIPEKVLRHFPLIPRLKRMFGSKELSAEAQWHKLKRKPVDNEL

SHPADGEAWKDFDRKYEWFANDARNVRLGLATDGFNPFGKMSSSYSMWPVFLIPYNF

PPWQCMEQSNFMMCLLIPGPTCPGKDMDLFLQPLVEELLNLWSGVPTLDALTGKEFDL

HAAIIWCIHDYPALSTLSGRVTRGYYACVCCDKNPCYKRLRNKICYIGHRRFLPVDHIW

RRKKDFNGQTEERAQPEEFTQDELMQQLARVEHVRPGNHPNNKKRKRVEEGQCWKRR

STLWDLPYWSNLKLRHNLDVMHIEKNICEALLGTFLDIAGKSKDSVTARLDLEDMGIRK

NLHLKDDGNSTCTALHAPYVMTKAQRKAFCAFIKNVKFPDGYASNLARCVSVDECKV

QALKTHDCHILLQRILPAGLRGIMHKEIYETIAELGNFFQQICAKKLKLDALNKMRGEIPII

LCKL

SEQ ID NO: 6 LOC_Os11g06410.1 SAB18 variant rice polypeptide
sequence The SANT domain is underlined.
M S I L L W L S H V L L K L H Y L R L Y S C A S S C T P V S I L Y G T N K K L K C L G D R F G E M E G S N P P G N M T Q G P S Y G S L D L H G I S K Q M H P P N S G N Q G F N Q P Q I P G N F T I P M D R V T E P D N I S D G V Q L G Q H G K I A H H H H H H R H H S K N H G S E E E E H D M N E D A A D G K D K K G S P W H R M K W T D S M V K L L I T A V S Y T G E D P G A D L G G G R R N Y S M M Q K K G K W K A I S K V M G E R G C H V S P Q R C E D K F N D L N K R Y K R L T D I L G R G T A C N V E N H S L L D H M D I S E K M K E D A R K I L N S K H L F Y E E M C S Y H N N N R I S L P E D P
```

ALQQSLQLALRCKEDNDFMRHASGDAELDDDQSEDSDYEENE

EEHRAVDTNIRGPSMHKRMWHVVDHGDVGFVTSCSNDGSRS

DPYDVLDINKPFPDGCDLALVQKDLALKAAEIQKHRLQIETKA

VQLAKQRLKWEMFRKN Stop

SEQ ID NO: 7-Nucleotide sequence encoding variant sequence SEQ ID NO: 6 The stop codon is underlined.

ATGTCTATCCTCCTTTGGCTATCCCATGTACTGCTGAAACTTCATTACTTGAGGTTAT

ATTCATGTGCATCCTCGTGCACTCCTGTGTCCATCTTATATGGTACCAACAAGAAGTT

GAAGTGTTTGGGTGATCGCTTTGGGGAAATGGAAGGCAGCAACCCACCTGGTAATA

TGACACAGGGACCTTCCTATGGGAGTTTAGATTTGCATGGTATCTCCAAGCAAATGC

ATCCTCCAAACTCAGGAAATCAGGGCTTCAACCAGCCTCAGATACCAGGGAATTTTA

CCATTCCTATGGATAGGGTTACAGAGCCTGATAACATCTCTGATGGAGTTCAGTTAG

GACAACATGGGAAGATTGCCCATCATCACCATCACCACAGACACCACTCAAAGAAC

CATGGGAGTGAGGAAGAGGAGCACGATATGAATGAGGATGCTGCTGATGGCAAAG

ACAAGAAGGGCTCTCCATGGCATCGGATGAAGTGGACAGATTCAATGGTGAAGCTT

TTGATTACTGCAGTATCCTACACAGGGGAGGATCCTGGAGCTGATTTAGGCGGTGGG

AGGAGGAACTATTCAATGATGCAAAAGAAGGGAAAATGGAAAGCAATATCAAAGG

TCATGGGCGAGAGAGGTTGCCATGTGTCGCCACAGCGGTGTGAGGATAAGTTCAAT

GACCTTAATAAGAGATACAAAAGACTAACAGATATCCTTGGAAGGGGTACTGCTTG

TAATGTTGTGGAGAATCACTCACTTCTTGATCACATGGATATTTCTGAGAAGATGAA

AGAGGATGCAAGGAAGATACTGAACTCCAAACACTTGTTCTATGAAGAGATGTGTT

CCTACCATAATAATAACCGTATAAGTCTGCCTGAAGATCCCGCACTTCAGCAGTCAC

TACAGCTTGCTCTTAGATGTAAAGAGGATAATGATTTCATGAGGCATGCAAGTGGAG

ATGCTGAACTAGATGATGATCAGAGTGAAGATTCAGATTATGAGGAGAATGAGGAA

GAACATCGAGCAGTTGATACCAATATAAGGGGCCCCTCAATGCATAAAAGGATGTG

GCATGTTGTAGATCATGGTGATGTAGGTTTTGTCACCTCATGCTCGAATGATGGTAG

TGGGAGGTCTGATCCCTATGACGTGTTGGATATCAACAAACCCTTTCCAGATGGATG

TGATTTGGCTTTGGTGCAAAAAGACTTGGCTCTGAAAGCAGCAGAGATTCAAAAAC

ATCGTTTGCAGATTGAAACCAAGGCTGTGCAACTCGCAAAGCAACGTCTCAAGTGG

GAGATGTTCAGGAAGAAC<u>TAG</u>GACTTGGAATTGGAAAAGTTGGCGTTGGAGAATGA

ACAAATGATGCTTCAGAATAAGCGGTTTGAGCTTGACCTAAGACACAAGGAGCTAG

AACTTGAGATTAAGATAAAGGGCAATGCTAATCATCCATGA

---

What is claimed is:

1. A plant comprising a recombinant nucleic acid comprising a promoter operatively linked to a polynucleotide encoding a SAB18 polypeptide, wherein the promoter is heterologous to the polynucleotide encoding the SAB18 polypeptide, and the SAB18 polypeptide comprises the amino acid sequence of SEQ ID NO:6 or amino acids 1-439 of SEQ ID NO:2; and further, wherein the plant overexpresses the SAB18 polypeptide relative to a corresponding native plant that has not been engineered to overexpress SAB18; and is tolerant to drought or submergence.

2. The plant of claim 1, wherein the SAB18 polypeptide comprises SEQ ID NO:6.

3. The plant of claim 1, wherein the plant is a grass plant.

4. The plant of claim 3, wherein the plant is a rice plant.

5. The plant of claim 1, wherein the plant comprises a polynucleotide that expresses a Sub1A polypeptide of SEQ ID NO:5.

6. A plant cell of the plant of claim 1.

7. A method for increasing tolerance of a plant to drought or submergence, the method comprising
   introducing into plants a nucleic acid comprising a polynucleotide encoding a SAB18 polypeptide comprising an amino acid sequence at least 95% identical to SEQ ID NO:6; wherein the polynucleotide encoding the SAB18 polypeptide is operatively linked to a promoter; and
   selecting a plant with increased drought tolerance or submergence tolerance compared to a plant lacking the nucleic acid.

8. The method of claim 7, wherein the promoter is heterologous to the polynucleotide encoding the SAB18 polypeptide.

9. The method of claim 7, wherein the SAB18 polypeptide comprises the amino acid sequence of SEQ ID NO:6 or amino acids 1-439 of SEQ ID NO:2.

10. The method of claim 7, wherein the plant is a monocot.

11. The method of claim 10, wherein the plant is a grass plant.

12. The method of claim 11, wherein the grass plant is a rice plant.

13. The method of claim 7, wherein the plant comprises a polynucleotide that expresses a Sub1A polypeptide of SEQ ID NO:5.

14. The method of claim 7, wherein the plant comprises a polynucleotide that expresses a Sub1A polypeptide of SEQ ID NO:5; and further, wherein the selecting step selects for submergence tolerance.

15. The method of claim 14, wherein the plant is a rice plant.

16. The method of claim 7, wherein: (i) the SAB18 polypeptide comprises the amino acid sequence of SEQ ID NO:6 or amino acids 1-439 of SEQ ID NO:2; (ii) the plant is a grass plant that comprises a polynucleotide that expresses a Sub1A polypeptide of SEQ ID NO:5; and (iii) the selecting step selects for submergence tolerance.

17. A plant having increased tolerance to drought or to submergence produced by the method of claim 7.

* * * * *